US011680277B2

(12) United States Patent
Banerjee

(10) Patent No.: US 11,680,277 B2
(45) Date of Patent: Jun. 20, 2023

(54) ARRAY OF NEEDLE MANIPULATORS FOR BIOLOGICAL CELL INJECTION

(71) Applicant: Mekonos Limited, Auckland (NZ)

(72) Inventor: Arunava Steven Banerjee, San Francisco, CA (US)

(73) Assignee: Mekonos Limited, Auckland (NZ)

( * ) Notice: Subject to any disclaimer, the term of this patent is extended or adjusted under 35 U.S.C. 154(b) by 963 days.

(21) Appl. No.: 16/346,525

(22) PCT Filed: Oct. 31, 2017

(86) PCT No.: PCT/NZ2017/050140
§ 371 (c)(1),
(2) Date: Apr. 30, 2019

(87) PCT Pub. No.: WO2018/080324
PCT Pub. Date: May 3, 2018

(65) Prior Publication Data
US 2019/0300907 A1    Oct. 3, 2019

(30) Foreign Application Priority Data

Oct. 31, 2016  (AU) ................................ 2016904437

(51) Int. Cl.
*C12N 15/89*      (2006.01)
*B01L 3/00*       (2006.01)
(Continued)

(52) U.S. Cl.
CPC ........ *C12N 15/89* (2013.01); *B01L 3/502761* (2013.01); *B25J 7/00* (2013.01);
(Continued)

(58) Field of Classification Search
CPC ......... C12N 15/89; C12M 3/00; C12M 23/12; C12M 23/50; C12M 33/06; C12M 35/00;
(Continued)

(56) References Cited

U.S. PATENT DOCUMENTS 5,114,854 A     5/1992  Bertholdt
5,262,128 A  *  11/1993  Leighton ................ C12M 23/50
                                                     422/522
(Continued)

FOREIGN PATENT DOCUMENTS

CN        105967138         9/2016
CN        105441325         12/2017
(Continued)

OTHER PUBLICATIONS

AU/RO—International Preliminary Report on Patentability of related International Application No. PCT/NZ2017/050140 dated May 9, 2019, 8 pgs.
(Continued)

*Primary Examiner* — Michael L Hobbs
(74) *Attorney, Agent, or Firm* — Jason Novak

(57) ABSTRACT

A device is provided, comprising a cell trap comprising a plurality of micro-chambers, each micro-chamber configured to hold a cell. The device can further comprise a manipulator array comprising a plurality of manipulators, each manipulator in spatial communication with a respective micro-chamber, wherein each manipulator comprises a needle, a stage, and an actuator, wherein the needle is mounted to the stage, and the actuator is operable to apply force to the stage in a direction to move the needle to penetrate a cell in the respective micro-chamber.

13 Claims, 33 Drawing Sheets

(51) Int. Cl.
  *B25J 7/00* (2006.01)
  *C12M 1/32* (2006.01)
  *C12M 1/00* (2006.01)
  *C12M 3/00* (2006.01)
(52) U.S. Cl.
  CPC .............. *C12M 3/00* (2013.01); *C12M 23/12* (2013.01); *C12M 23/50* (2013.01); *C12M 33/06* (2013.01)
(58) Field of Classification Search
  CPC .... B01L 3/502761; B25J 7/00; B81B 3/0062; B81B 2201/033; B81B 2201/055
  See application file for complete search history.

(56) References Cited

U.S. PATENT DOCUMENTS

| | | | |
|---|---|---|---|
| 6,264,815 | B1 | 7/2001 | Pethig et al. |
| 6,475,760 | B1 | 11/2002 | Baumann et al. |
| 6,645,757 | B1 | 11/2003 | Okandan et al. |
| 7,501,276 | B2 | 3/2009 | Baumann et al. |
| 7,872,394 | B1 | 1/2011 | Gritters et al. |
| 9,987,427 | B1 | 6/2018 | Polsky et al. |
| 2001/0008961 | A1 | 7/2001 | Hecker et al. |
| 2003/0015807 | A1* | 1/2003 | Montemagno .... A61M 37/0015 438/689 |
| 2004/0185592 | A1 | 9/2004 | Bergaud et al. |
| 2006/0072187 | A1 | 4/2006 | McKinnell et al. |
| 2007/0087436 | A1 | 4/2007 | Miyawaki et al. |
| 2007/0019422 | A1 | 8/2007 | Zorn |
| 2007/0194225 | A1 | 8/2007 | Zorn |
| 2007/0220882 | A1 | 9/2007 | Culpepper et al. |
| 2009/0166896 | A1 | 7/2009 | Yamazaki et al. |
| 2009/0198189 | A1 | 8/2009 | Simons et al. |
| 2009/0291502 | A1 | 11/2009 | Tateyama |
| 2011/0262891 | A1 | 10/2011 | Ozaki et al. |
| 2012/0225435 | A1 | 9/2012 | Seger et al. |
| 2013/0023052 | A1 | 1/2013 | Tanaka |
| 2013/0045530 | A1* | 2/2013 | Gracias ............... B81C 1/00007 428/57 |
| 2013/0077945 | A1 | 3/2013 | Liu et al. |
| 2014/0323837 | A1 | 10/2014 | Hirshberg |
| 2016/0066789 | A1 | 3/2016 | Rogers et al. |
| 2016/0252546 | A1 | 9/2016 | Amponsah |
| 2019/0300907 | A1 | 10/2019 | Banerjee |
| 2020/0150141 | A1* | 5/2020 | Banerjee ........... G01N 35/00584 |

FOREIGN PATENT DOCUMENTS

| | | |
|---|---|---|
| CN | 110418844 | 11/2019 |
| EP | 1999465 | 11/2016 |
| EP | 2494332 | 8/2018 |
| TW | 425294 | 3/2001 |
| WO | WO-0177001 A2 * | 10/2001 ............ B81B 3/004 |
| WO | WO 2007/007058 | 1/2007 |
| WO | 2008034249 A1 | 3/2008 |
| WO | WO-2011103143 A1 * | 8/2011 ......... B01J 19/0046 |
| WO | 2013126556 A1 | 8/2013 |
| WO | 2014090415 A1 | 6/2014 |
| WO | WO-2014090415 A1 * | 6/2014 ............ C12M 23/04 |
| WO | WO 2016/019250 | 2/2016 |
| WO | WO 2018/080324 | 5/2018 |

OTHER PUBLICATIONS

AU/RO—International Preliminary Report on Patentability of related International Application No. PCT/NZ2017/050141 dated May 9, 2019, 12 pgs.
AU/RO—International Search Report of related International Application No. PCT/NZ2017/050141 dated Mar. 14, 2018, 18 pgs.
Office Action issued in Corresponding Korean Application No. 10-2019-7015608, dated Feb. 23, 2022 (English Translation provided).
AU/RO—International Search Report of related International Application No. PCT/NZ2017/050140 dated Feb. 19, Jul. 2018, 11 pgs.
AU/RO—Republication (A9) of related International Application No. PCT/NZ2017/050140 dated Apr. 18, 2019, 87 pgs.
Supplementary European Search Report from European Patent Application No. EP17863767.4, dated May 4, 2020, 8 pages.
Search Report and Written Opinion from Singapore Patent Application No. 11201903797S, dated Jul. 1, 2020, 9 pages.
Office Action in corresponding Australian Patent Application No. 2020290475, dated Sep. 13, 2022.
Office Action in corresponding Chinese Application No. 2017800810960, dated Nov. 25, 2022.
Office Action in corresponding Chinese Application No. 201780080583.5, dated Nov. 25, 2022.
Search Report and Written Opinion from related Singapore Patent Application No. 11201903750R, dated Jun. 23, 2020, 14 pages.
European Search Report dated Jun. 3, 2020 issued in co-pending European Patent App. No. 17864076.9, 6 pages.
Office Action issued in corresponding Chinese Application No. 202080042578.7, dated Feb. 3, 2023.
Office Action issued in corresponding Chinese Application No. 2017/80080583.5, dated Nov. 25, 2022.
Office Action issued in corresponding Canadian Application No. 3,138,947, dated Jan. 4, 2023.
Office Action issued in corresponding Australian Application No. 2017349494, dated Jan. 30, 2023.

* cited by examiner

ARRAY OF NEEDLE MANIPULATORS FOR BIOLOGICAL CELL INJECTION

CROSS-REFERENCE OF RELATED APPLICATIONS

This is the national stage application filed under 35 U.S.C. § 371 of International Application PCT/NZ2017/050140, filed Oct. 31, 2017, which designated the United States of America, the disclosure of which is incorporated herein by reference, which claims the benefit Australian Application No. 2016904437, filed Oct. 31, 2016, the entire contents of which are hereby incorporated by reference.

FIELD

This disclosure relates to improvements in respect of manipulation via needles for injecting biological cells.

BACKGROUND

Injecting biological cells can be achieved by using a microneedle or nanoneedle to penetrate the cell to deliver an agent to be injected. Conventional approaches involve using a device to move the needle in 3-D. Conventional devices use micro-engineered machine (MEMS) technologies involving devices formed from silicon wafer.

There is an accepted need to make biological cell injection operation as cost-effective as possible, and to provide an array of needle manipulators which results in improved throughput of biological cell injection operations and is readily controllable.

The applicant has observed potential advantage in a number of devices in parallel on a single silicon wafer.

The applicant has observed a potential advantage in controlling a number of devices in parallel on a single silicon wafer.

SUMMARY

In an embodiment, a device is provided, comprising a cell trap comprising a plurality of micro-chambers, each micro-chamber configured to hold a cell. The device can further comprise a manipulator array comprising a plurality of manipulators, each manipulator in spatial communication with a respective micro-chamber, wherein each manipulator comprises a needle, a stage, and an actuator, wherein the needle is mounted to the stage, and the actuator is operable to apply force to the stage in a direction to move the needle to penetrate a cell in the respective micro-chamber.

Alternatively, each can manipulator comprises a plurality of actuators operable to apply a plurality of forces to the stage in a plurality of directions to move the needle.

Alternatively, the manipulator array can comprise a plurality of sub-arrays, each sub-array comprising a portion of the plurality of manipulators. At least one sub-array of the plurality of manipulators can be three-sided. At least one sub-array substantially can form a triangle. Alternatively, the sub-arrays are arranged to substantially form a hexagon.

The manipulator array can further comprise an interconnect, wherein the interconnect comprises connections to the actuator. Alternatively, the manipulator array further comprises a plurality of interconnects, wherein each interconnect comprises connections to the actuator, and wherein each interconnect is associated with a manipulator. The interconnect can comprise a local interconnect, a transitional interconnect and a universal interconnect, wherein the universal interconnect is connected to the transitional interconnect, and the transitional interconnect is connected to the local interconnect. Alternatively, the interconnect is located substantially at a side of the manipulator array. Alternatively, the interconnect is located substantially at a periphery of the manipulator array.

In another embodiment, a manipulator array is provided comprising a substrate, a plurality of manipulators arranged on the substrate, and a plurality of sub-arrays. Each manipulator can comprise a needle, a stage, a tether, and an actuator, wherein the needle is mounted to the stage, the stage is connected to the actuator by the tether, and the actuator is operable to apply tension in at least one axis to actuate the stage in a direction to manipulate the needle. Each sub-array can comprise a portion of the plurality of manipulators, and interconnects formed on each side of each sub-array, wherein the plurality of sub-arrays are arranged together on the substrate with at least a portion of the interconnects located at a periphery of the manipulator array.

Alternatively, each manipulator comprises a plurality of actuators operable to apply tension in more than one axis to actuate the stage in a direction to manipulate the needle.

Alternatively, at least one sub-array of the plurality of manipulators is three-sided. At least one sub-array can substantially form a triangle. Alternatively, the sub-arrays are arranged to substantially form a hexagon.

Alternatively, the interconnects comprise connections to the actuator, and wherein each interconnect is associated with a manipulator. The interconnects can comprise a local interconnect, a transitional interconnect and a universal interconnect, wherein the universal interconnect is connected to the transitional interconnect, and the transitional interconnect is connected to the local interconnect.

Alternatively, the plurality of actuators are operable to apply tension in three directions. Alternatively, the plurality of actuators is operable to provide tensile forces.

Alternatively, the manipulator array is operable to receive applied voltages at the interconnect, the voltages generating electrostatic forces to cause the actuator to apply tension so as to actuate the stage parallel to a plane parallel with the manipulator array to manipulate the needle.

Alternatively, the manipulator array is operable to receive applied voltages at the interconnect, the voltages generating electrostatic forces to cause the actuator to apply tension so as to actuate the stage transverse to a plane parallel with the manipulator array to manipulate the needle.

Alternatively, the manipulator array is operable to receive applied voltages at the interconnect at a periphery of the device, the voltages generating electrostatic forces to cause the actuator to apply forces so as to actuate the stage parallel to a plane parallel with the manipulator to move the needle with respect to the associated micro-chamber of the cell trap.

Alternatively, the manipulator array is operable to receive applied voltages at the interconnect at a periphery of the device, the voltages generating electrostatic forces to cause the actuator to apply forces so as to actuate the stage transverse to a plane parallel with the manipulator to move the needle with respect to the associated micro-chamber of the cell trap.

BRIEF DESCRIPTION OF THE DRAWINGS

Additional and further aspects of the present invention will be apparent to the reader from the following description of embodiments, given in by way of example only, with reference to the accompanying drawings in which.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

The following description of various embodiments is exemplary and explanatory only and is not to be construed as limiting or restrictive in any way. Other embodiments, features, objects, and advantages of the present teachings will be apparent from the description and accompanying drawings, and from the claims.

As used herein, the terms "comprise", "comprises", "comprising", "contain", "contains", "containing", "have", "having" "include", "includes", and "including" and their variants are not intended to be limiting, are inclusive or open-ended and do not exclude additional, unrecited additives, components, integers, elements or method steps. For example, a process, method, system, composition, kit, or apparatus that comprises a list of features is not necessarily limited only to those features but may include other features not expressly listed or inherent to such process, method, system, composition, kit, or apparatus As used herein the term 'substantially form a triangle' or similar refers generally to shape which has a base suitable for providing a relatively wide side suitable for providing an electrical interconnect and has a relatively narrow end compared to the wide area, such as an apex in one example, which is suitable for arranging beside similar shapes to pack the shapes more densely than allowed by the relatively wide side providing an interconnect.

As used herein the term 'substantially form a hexagon' refers generally to a six-sided shape which allows packing of shapes with a relatively wide base suitable for providing an electrical interconnect and with adjacent sides at acute angles to the relatively wide base, such as the triangle in one example.

As used herein the term 'mounted' refers generally to any means by which a needle is located or connected to an actuation stage, including forming the needle integrally with the actuation stage.

As used herein the phrase 'in a direction' refers generally to a direction of force respect of whether that force is applied using tension in a given direction, compression, stress or other means known to the reader.

As used herein the phrase 'manipulate', 'manipulator' or the like refers generally to moving a needle such as to locate the needle with respect to a biological cell for penetration of the cell by the needle.

Figure 1:
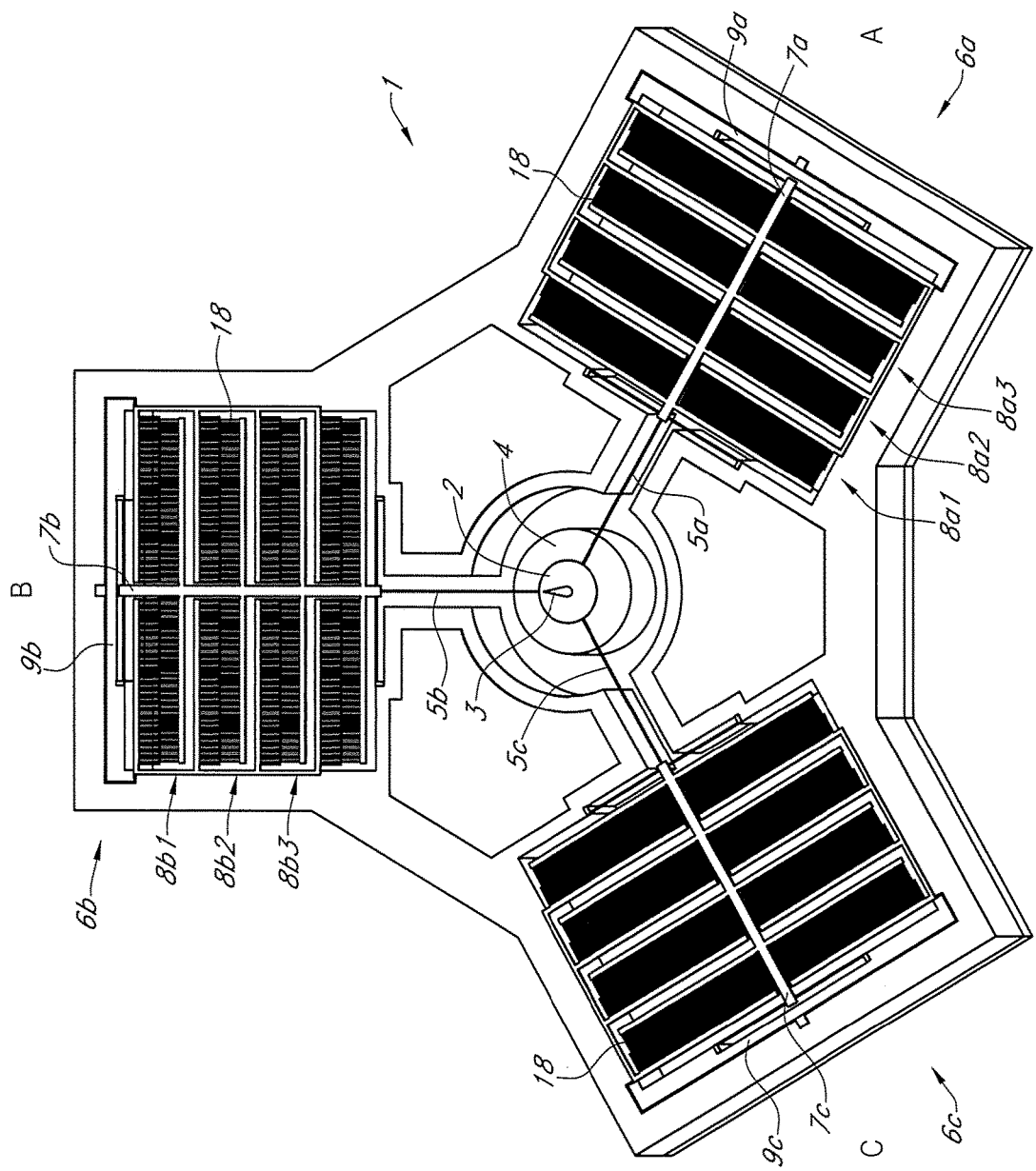
FIG. 1 illustrates a single-unit manipulator with three actuators included in an array of needle manipulators, in accordance with various embodiments.

FIG. 1 illustrates a nanorobot or microrobot in the form of a single-unit needle manipulator 1 which is included in an array of needle manipulators in accordance with various embodiments, the features of which can be used as illustrated or in combination with other embodiments disclosed herein.

The single-unit manipulator 1 has a manipulation stage 2 on which a needle 3 is mounted. Needle 3 can be of a type suited to penetrate an object or cell to deliver, or inject, an agent to the object or cell interior. The injected object or cell may be a biological cell, wherein needle 3 can be of a type suited to penetrate biological cells to deliver, or inject, an agent to the cell interior and/or cell nucleus.

The stage 2 can be located above a tower 4 which can be electrically charged relative to the stage 2 to apply electrostatic forces to the stage 2. The stage and tower may be referred to collectively as a parallel-plate actuator, wherein the opposing surfaces on the stage and tower are electrostatically charged when a voltage is applied across them. Electrostatic forces between the tower 4 and stage 2 can actuate the stage 2 in a Z-axis.

As will be described in detail below in reference to FIG. 28, Z-axis actuation may be the only actuation needed to provide the movement necessary to affect appropriate cell or object penetration by needle 3.

This Z-axis can be considered the central axis of the tower 4 as shown in FIG. 1. The stage 2 can also be actuated in different axes lying in an X-Y plane, in the plane of the manipulator 1 as shown in FIG. 1, by tethers 5a, 5b and 5c. Stage 2 can be configured to manipulate a needle 3 suitable for penetration of objects on this scale of a biological cell. As such, the stage 2 may be referred to as a micro-stage or nano-stage.

The tethers 5a, 5b and 5c tether the stage 2 to actuators 6a, 6b and 6c respectively. The actuators 6 can be located so that forces transferred by the tethers 5 can be in three different axes in the X-Y plane. Each tether 5a/5b/5c can apply tensile forces. Actuators 6 can serve to apply forces from three different directions A, B and C. For example, the actuators 6 can be arranged at 120° intervals about stage 2.

Tether beams 7a, 7b and 7c of actuators 6a, 6b and 6c can connect each of tethers 5a, 5b and 5c to three support beams 8. The support beams 8 support comb-features, or comb-like electrostatic actuators (not shown). For example, the actuator 6a can have support beams 8a1, 8a2, and 8a3. Actuators 6a and 6c similarly have support beams 8b1/8b2/8b3 and 8c1/8c2/8c3 respectively.

Figure 2:
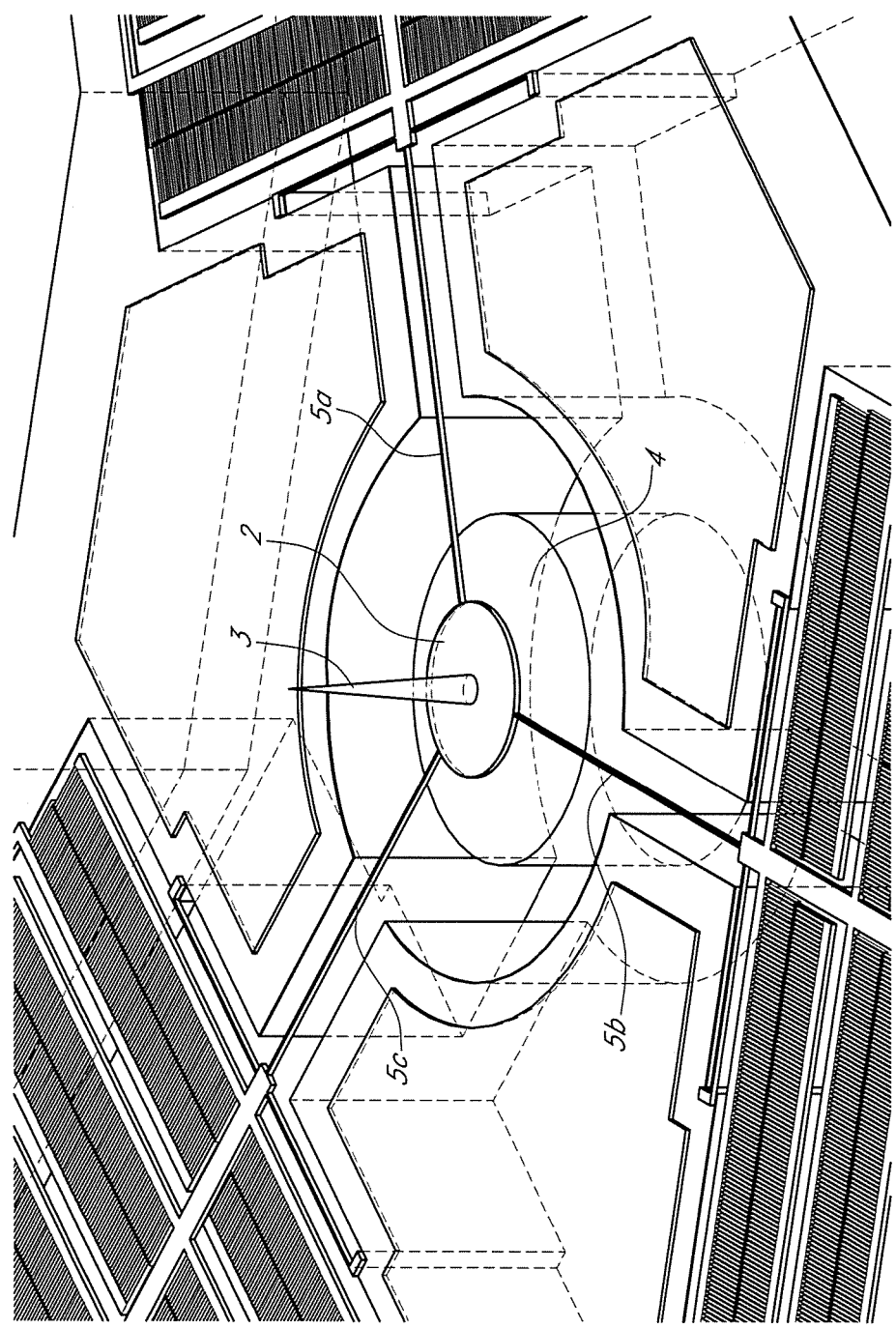
FIG. 2 illustrates an actuation stage of a single-unit manipulator, in accordance with various embodiments.

FIG. 2 illustrates a portion of the single-unit manipulator, such as that illustrated, for example, in FIG. 1, in accordance with various embodiments, the features of which can be used as illustrated or in combination with other embodiments disclosed herein. Electrostatic comb features (not shown) can be located in the same plane as the support beams 8 shown, for example, in FIG. 1. The comb-features may be referred to as comb-drive actuators or comb-drives. The comb-features (not-shown) can be configured to apply force on the support beams 7 in the X-Y axis. The parallel-plate actuator including the central micro-stage 2 and the tower 4 underneath it can be configured to apply force on the tethers 5 in the Z axis. The actuators can have a set of comb-features (not shown) on the support beams 8 and another opposing set of comb-features (not shown) on the manipulator body. The two opposing sets of comb-features can be charged relative to each other to generate an electrostatic force in the X-Y axis, providing a comb-drive. Similarly the opposing micro-stage 2 and the tower 4 of the parallel-plate actuator can be charged relative to each other to generate an electrostatic capacitive force in the Z axis.

Spring-flexure beams 9a, 9b and 9c connect and anchor support beams 8a, 8b and 8c to the substrate 10 of the manipulator 1. The spring-flexure beams 9, by nature of their stiffness, generate mechanical forces to allow support beams 8 and tethers 7 to move.

Spring-flexure beams 9a/9b/9c can be configured and aligned to connect and anchor support beams 8a, 8b and 8c to a substrate 10 of the manipulator 1. The spring-flexure beams 9 allow the support beams 8 and tethers 7 to move under the effect of the actuators 6. Tension applied to the stage 2 by a tether 5 connected to a respective actuator 6 can apply a force to the stage 2 in the direction of the respective actuator 6. Control of the forces applied to the stage 2 in the direction of each actuator 6 individually allows the stage 2 to be actuated so as to manipulate the needle 3. In so doing, tethers 5 can stretch, and movement of the stage 2 can be dependent on stretching, or strain, of the tethers 5 as well as flexing of the spring-flexure beams 9.

As shown in FIG. 2, for example, the three tethers 5 of the single-unit manipulator connect actuators in three respective directions to a central stage to provide an elastic support structure for the stage 2.

As further shown in FIG. 2, for example, three support beams 8, provided for each actuator 6 of the single-unit manipulator 1, provide a support structure to hold the opposing comb-features and can act as a connecting element between spring-flexure beams 9 and tether beams 7, which are connected to tethers 5.

Figure 3:
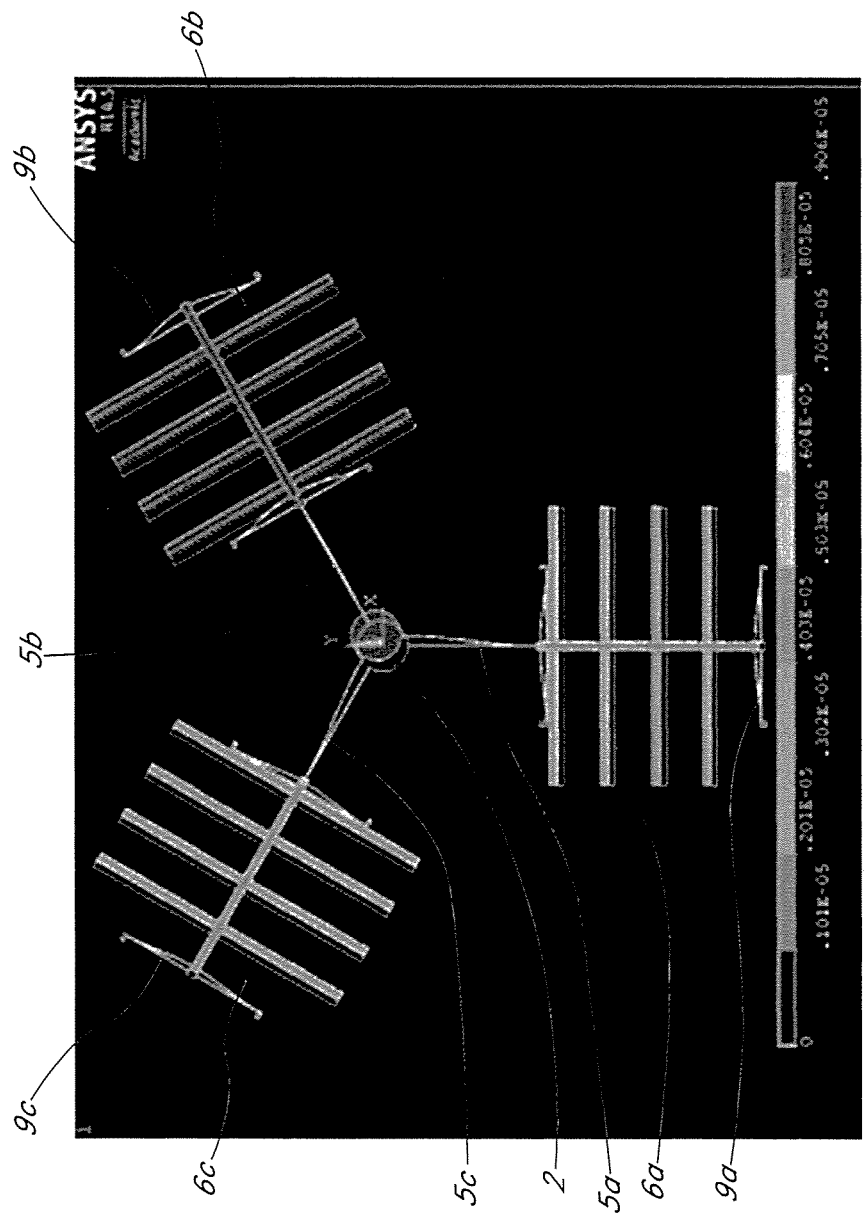
FIG. 3 illustrates actuators applying forces to an actuation stage from three different directions, in accordance with various embodiments.

FIG. 3 illustrates a single-unit manipulator 1 with actuators 6a, 6b and 6c, in accordance with various embodiments, the features of which can be used as illustrated or in combination with other embodiments disclosed herein. In FIG. 3, the actuator 6b is activated to pull support beams 8a while 6a and 6c are not activated. The effect shown in FIG. 3 is to manipulate the needle 3 mounted on the stage 2 in the direction of the actuator 6b. Similar or equivalent effects might also be achieved by each of the actuators 6 being activated with actuator 6b being activated by a greater degree relative to the others. Similarly, the stage 2 can be actuated by electrostatic charges on the front face of the tower 4, or by the parallel-plate actuator, to manipulate the needle 3 downward into the page (not shown).

Figure 4:
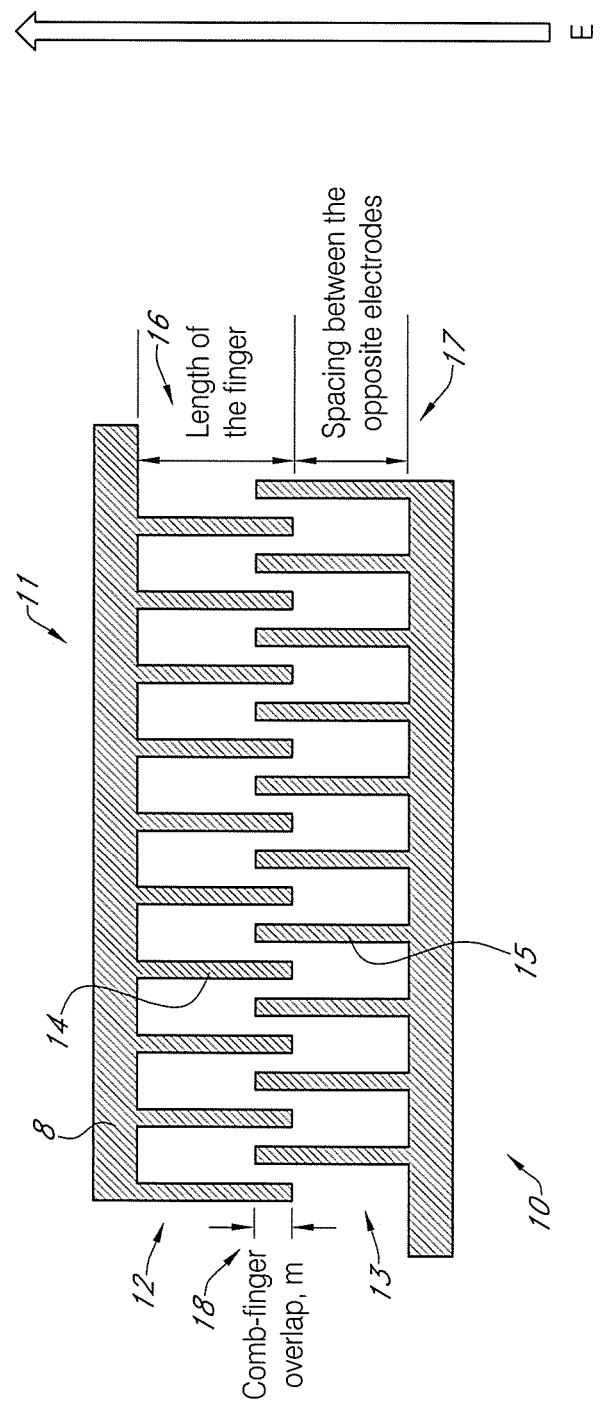
FIG. 4 schematically illustrates comb-features of the actuators of FIG. 3, in accordance with various embodiments.

FIG. 4 gives a schematic illustration of a comb-drive 11, in accordance with various embodiments, the features of which can be used as illustrated or in combination with other embodiments disclosed herein. The comb-drive 11 can include a movable comb 12, which can be mounted on support beam 8. The comb-drive 11 can also include a fixed comb 13, which can be mounted on the substrate 10 of manipulator 1. The movable comb 12 can include a set of fingers 14. As illustrated, a set of opposing and offset fingers 15 can be provided on the fixed comb 13. Offsetting the fingers 15 from fingers 14 can allow both sets of fingers to be drawn together to overlap in the X-Y axis.

FIG. 4 further illustrates a length 16 of the fingers, which can be the same for each set 14 and 15, but may differ in length as desired. FIG. 4 also illustrates a spacing 17 between opposite combs 12 and 13 and an overlap 18 of opposite combs 12 and 13. The combs 12 and 13 can form electrodes that can form electric fields to draw the combs 12 and 13 towards each other if the combs 12 and 13, acting as electrodes, are electrostatically charged relative to each other. Accordingly, suitable control of the relative electrostatic charge on the combs 12 and 13 can control the force of the movable comb 12 in direction E. This provides a mechanism for actuation for the manipulator 1 provided by actuators 6.

Figure 5:
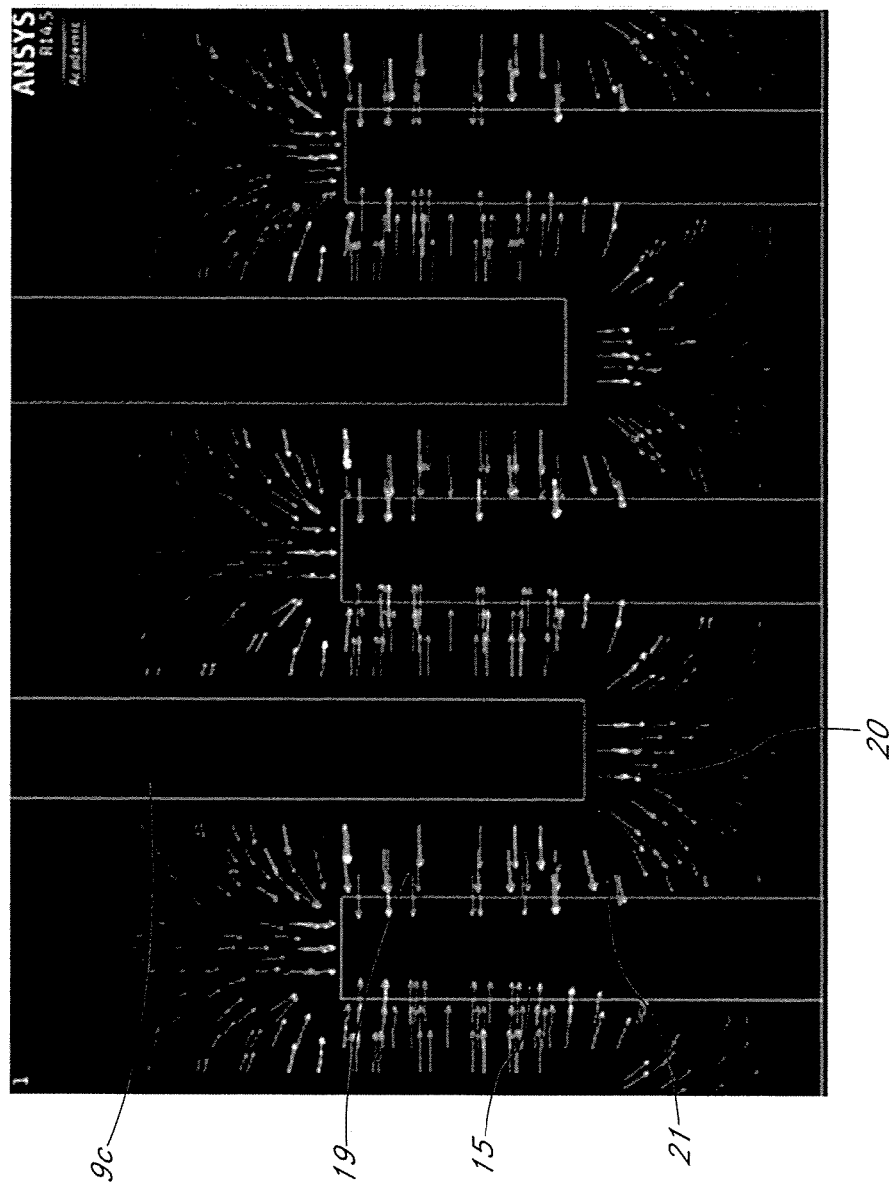
FIG. 5 illustrates electrostatic fields generated in the comb-features, in accordance with various embodiments.

FIG. 5 illustrates electric fields generated by electrostatic charges applied to fingers 14 relative to fingers 15, in accordance with various embodiments, the features of which can be used as illustrated or in combination with other embodiments disclosed herein. Specifically, FIG. 5 shows fields 19 attracting overlapping parts of fingers 14 and 15. Also shown in FIG. 5 are fields 20 between the ends of fingers 14 or 15 and fields 21 between fingers 14 or 15 and sides of fingers 15 or 14. Since fields 19 and 21 attract fingers 15, they can cancel each other's effect, leaving, for example, an axial back-and-forth motion of the fingers, thus pulling the support beams 8, tethering beam 7, tethers 5 and stage 2. The electrostatic charges can be applied via support beams 8 and the substrate 10.

The fingers 14 form part of the comb 12, which are mounted on the support beam 8, while the fingers 15 form part of the comb 13, mounted on the substrate 10. The electrical fields illustrated correspond to a difference in charge, or opposite charge, applied to the combs 12 and 13.

Figure 28:
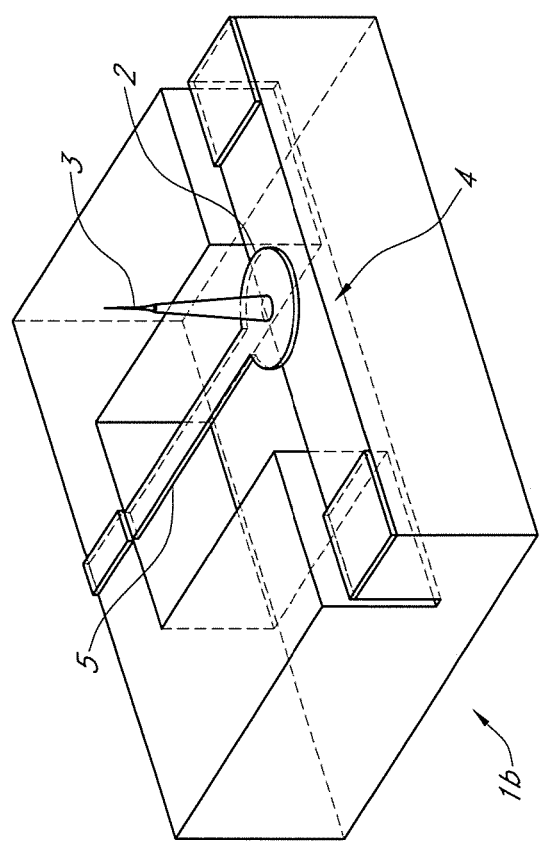
FIG. 28 illustrates a single-unit manipulator with a single actuator included in an array of needle manipulators, in accordance with various embodiments.

FIG. 28 illustrates a nanorobot or microrobot in the form of a single-unit needle manipulator 1b which is included in an array of needle manipulators in accordance with various embodiments, the features of which can be used as illustrated or in combination with other embodiments disclosed herein.

The single-unit manipulator 1b has, as discussed above, a manipulation stage 2 on which a needle 3 is mounted. Needle 3 can be of a type suited to penetrate an object or cell to deliver, or inject, an agent to the object or cell interior. The injected object or cell may be a biological cell, wherein needle 3 can be of a type suited to penetrate biological cells to deliver, or inject, an agent to the cell interior and/or cell nucleus.

As discussed above, the stage 2 can be located above a pillar, or tower, 4 which can be electrically charged relative to the stage 2 to apply electrostatic forces to the stage 2. Stage 2 and pillar 4 can form a parallel-plate actuator. Electrostatic forces between the pillar 4 and stage 2 can actuate the stage 2 in a Z-axis causing vertical displacement of the stage 2 relative to the stage 4 and actively deflecting the tether (of cantilever beam) 5. This Z-axis can be considered the central axis of the pillar 4 as shown in FIG. 28. Further, as illustrated, the Z-axis actuator is the only actuator shown as it provides the movement necessary to affect appropriate cell or object penetration by needle 3. This single actuation provides advantages as discussed in detail herein. Single axis actuation is particularly useful when an accompanying cell trap (as discussed in detail below) enables close control of the cell or object provided within its micro chambers (as discussed in detail below) such that Z-axis actuation provides all requisite movement necessary for needle penetration of the trapped cell.

Figure 29:
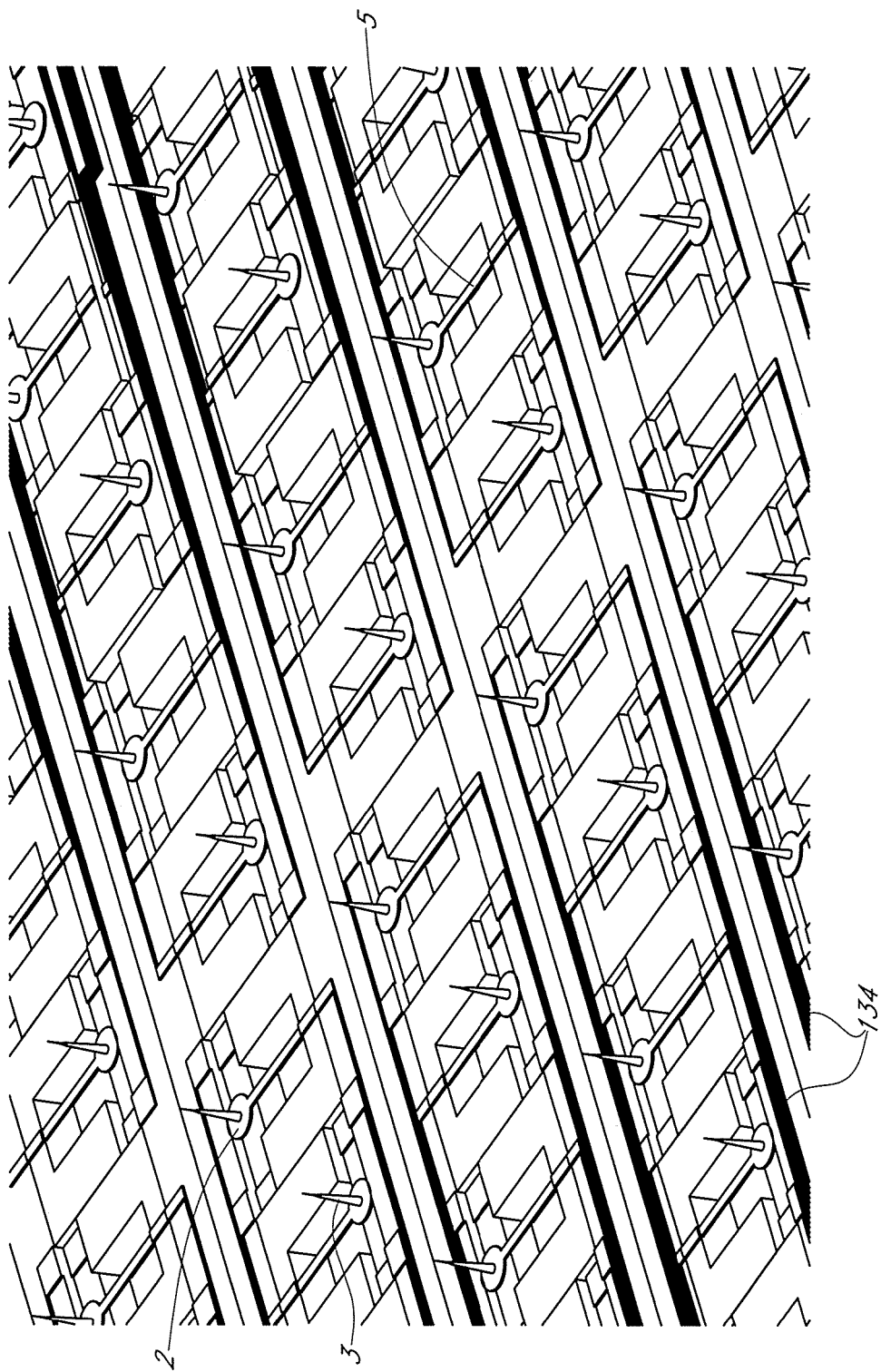
FIG. 29 illustrates an array of needle manipulators, in accordance with various embodiments.

FIG. 29 illustrates a possible architecture for packing and electrically connecting single-unit manipulators 1b onto a wafer using metal interconnects 134, in accordance with various embodiments, the features of which can be used as illustrated or in combination with other embodiments disclosed herein.

Figure 6:
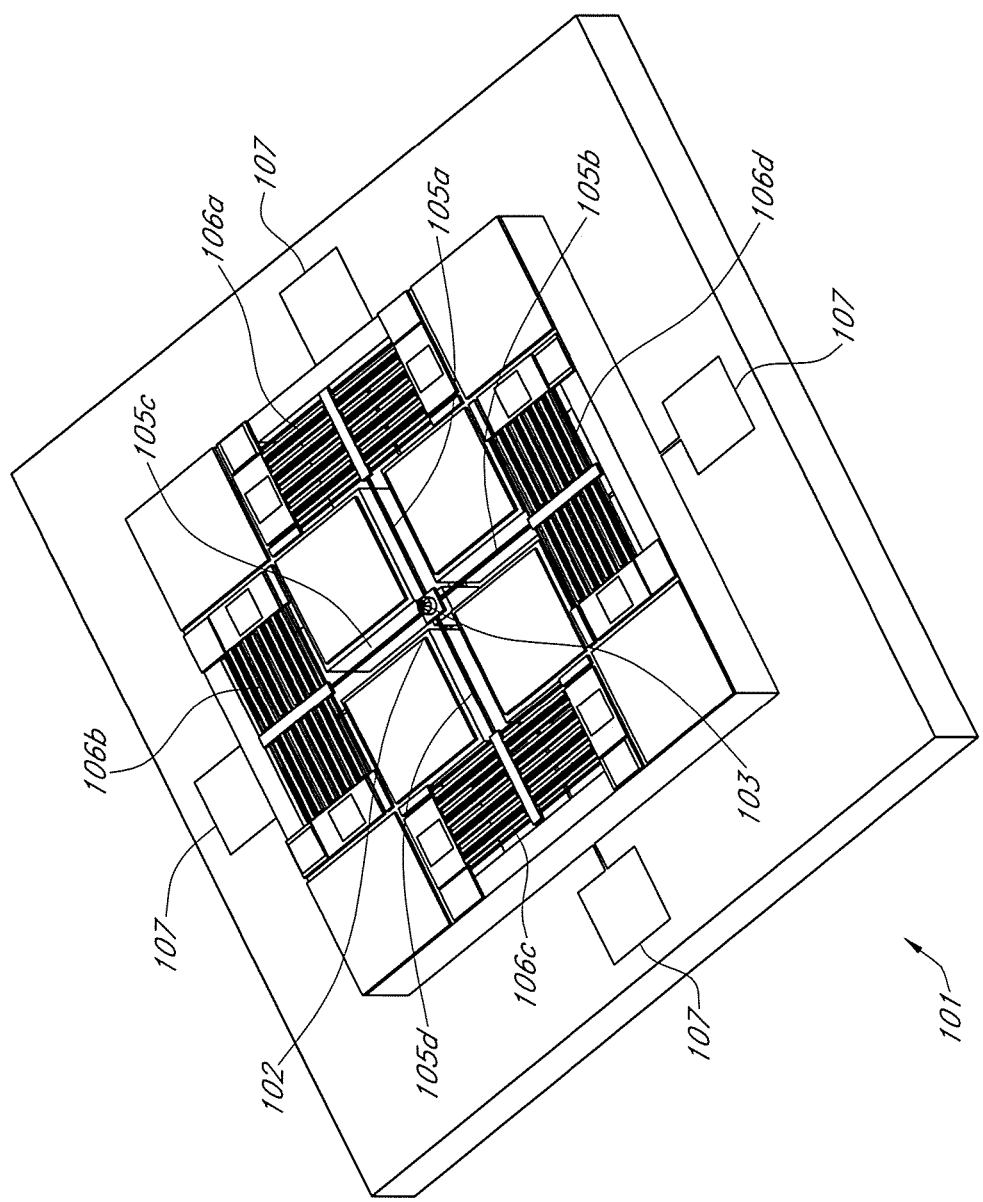
FIG. 6 illustrates a single-unit manipulator with four actuators included in an array of needle manipulators, in accordance with various embodiments.

FIG. 6 illustrates a needle manipulator 101, in accordance with various embodiments, the features of which can be used as illustrated or in combination with other embodiments disclosed herein. The needle manipulator 101 has a stage 102 on which a needle 103 is mounted. Tethers 105a to 105d tether the stage 102 to four actuators 106a to 106d. The manipulator 101 of FIG. 6 has 4 actuators arranged in two orthogonal axes, such as X-axis and Y-axis, for example, as two pairs of opposing actuators 106. As shown in FIG. 6, the manipulator 101 has an approximately square footprint, and the stage 102 and needle 103 are manipulated by opposing tension forces from each of the pair of actuators 106a and 106c and also by opposing tension forces from the opposing pair of actuators 106b and 106d. The metal pads 107 provide the electrical connections to the manipulator 101.

Figure 7:
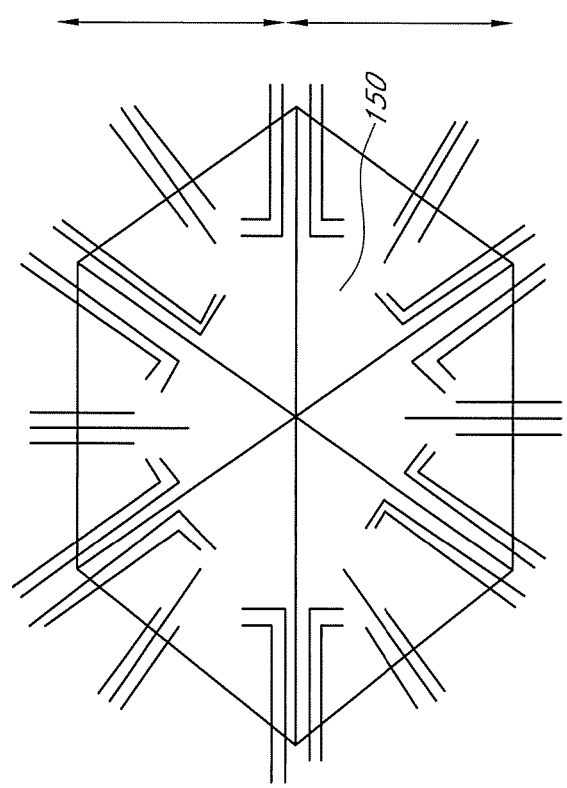
FIG. 7 schematically illustrates a packing density of needle manipulators in an array of needle manipulators, in accordance with various embodiments.

FIG. 7 illustrates how single unit manipulators 1 such as that illustrated, for example, in FIG. 1 can be packed into an array 150 of manipulators, in accordance with various embodiments, the features of which can be used as illustrated or in combination with other embodiments disclosed herein. In order to densely pack the electrical interconnects corresponding to the microrobots efficiently, the effect of electrical coupling can be considered. Their generally exists a minimum distance between these electrical interconnects before electrical coupling prevails. That minimum distance can be, for example, around 30 nm. Therefore, considering an array with six microrobots, for example, the single unit manipulator with three actuators have 42 electrical connections and occupy at least 43% less surface area compared to the single unit manipulator with four actuators, which have 54 electrical connections. Thus, in terms of the size, a transition of single unit manipulators from four-sided to three-sided actuators not only can reduce the number of electrical interconnects on every side by two, but also can increase the density of microrobots that can be packed into a single parallel architecture.

Figure 8:
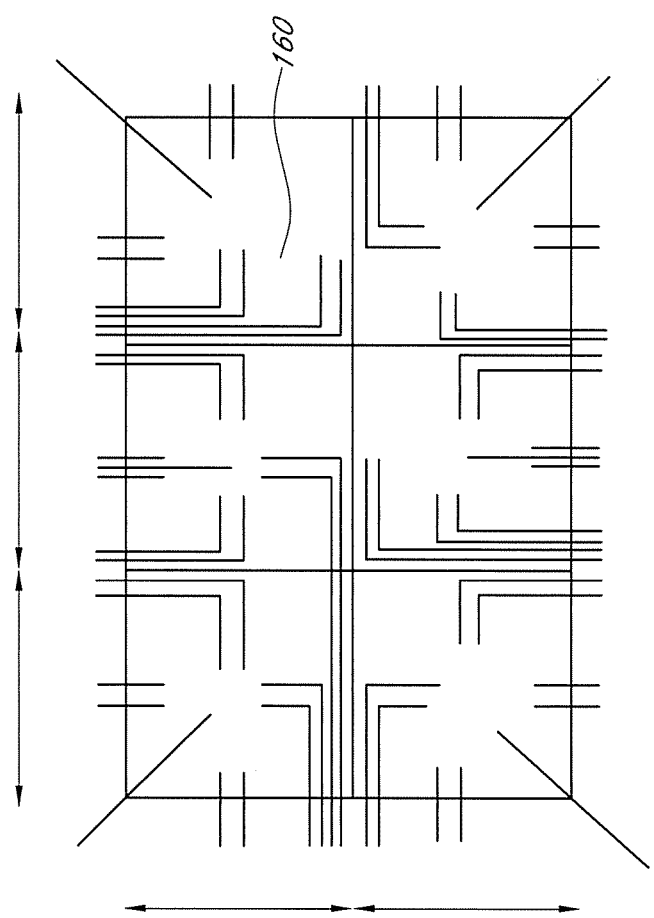
FIG. 8 schematically illustrates a packing density of needle manipulators in an array of needle manipulators, in accordance with various embodiments.

FIG. 8 illustrates how single unit manipulators 101 such as that illustrated, for example, in FIG. 6 can be packed into an array 155 of manipulators, in accordance with various embodiments, the features of which can be used as illustrated or in combination with other embodiments disclosed herein.

Figure 9C:
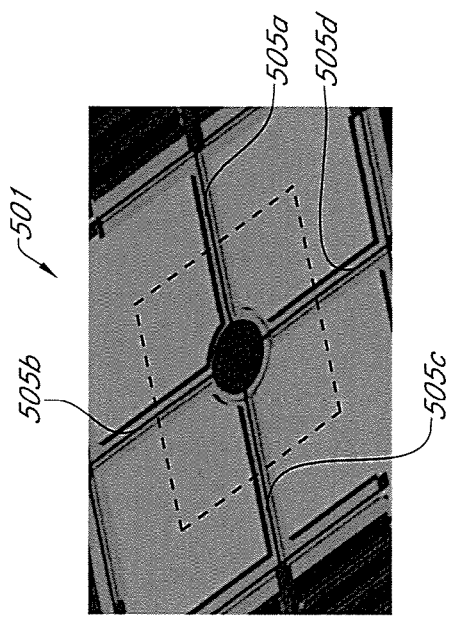
FIGS. 9a, 9b and 9c illustrate axes of force of a single-unit manipulator, in accordance with various embodiments.
Figure 9B:
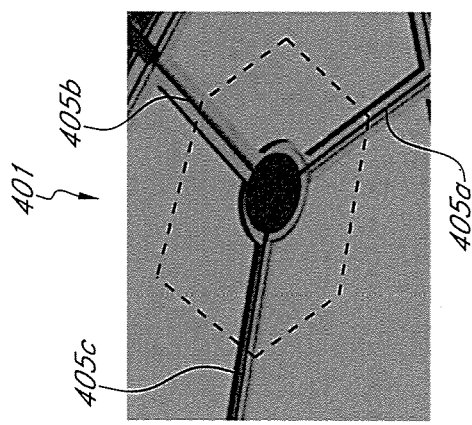
Figure 9A:
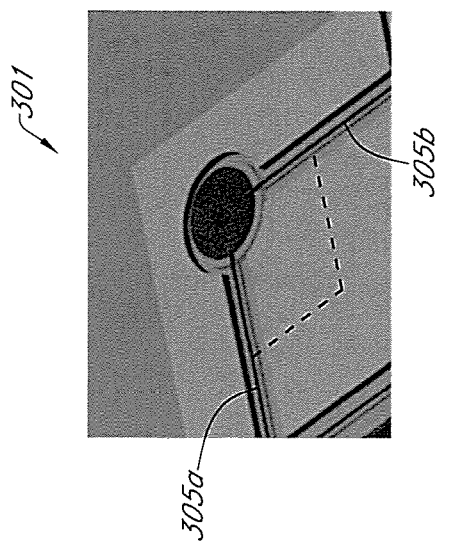

FIGS. 9a, 9b and 9c illustrate three single-unit manipulators, in accordance with various embodiments, the features of which can be used as illustrated or in combination with other embodiments disclosed herein. FIG. 9a shows a manipulator 301 with tethers 305a and 305b connected to actuators (not shown) arranged so that the tethers 305a and 305b are orthogonal. FIG. 9b illustrates a single-unit manipulator 401, similar to single-unit manipulator 1 of FIG. 1, with tethers 405a, 405b and 405c. FIG. 9c shows a single-unit manipulator 501, similar to single-unit manipulator 101 of FIG. 6, with tethers 505a, 505b, 505c and 505d. Having a two-sided actuator in a single-unit manipulator as illustrated, for example, in FIG. 9a, the zone of actuation of the nano-needle almost reduces to 50% in contrast to the achievable motion with the other two actuator designs. With the two-sided actuator, because of the pull-mode, the nanoneedle can move in only one-half direction of x and y axes which significantly limits its motion. With the other two actuator designs, because of pull-pull mode, the actuation zone covers the entire x and y axes. In other variations of the manipulator design, adding extra sides will continue increasing the spring stiffness of the system and will result in decreasing motion range.

Figure 10:
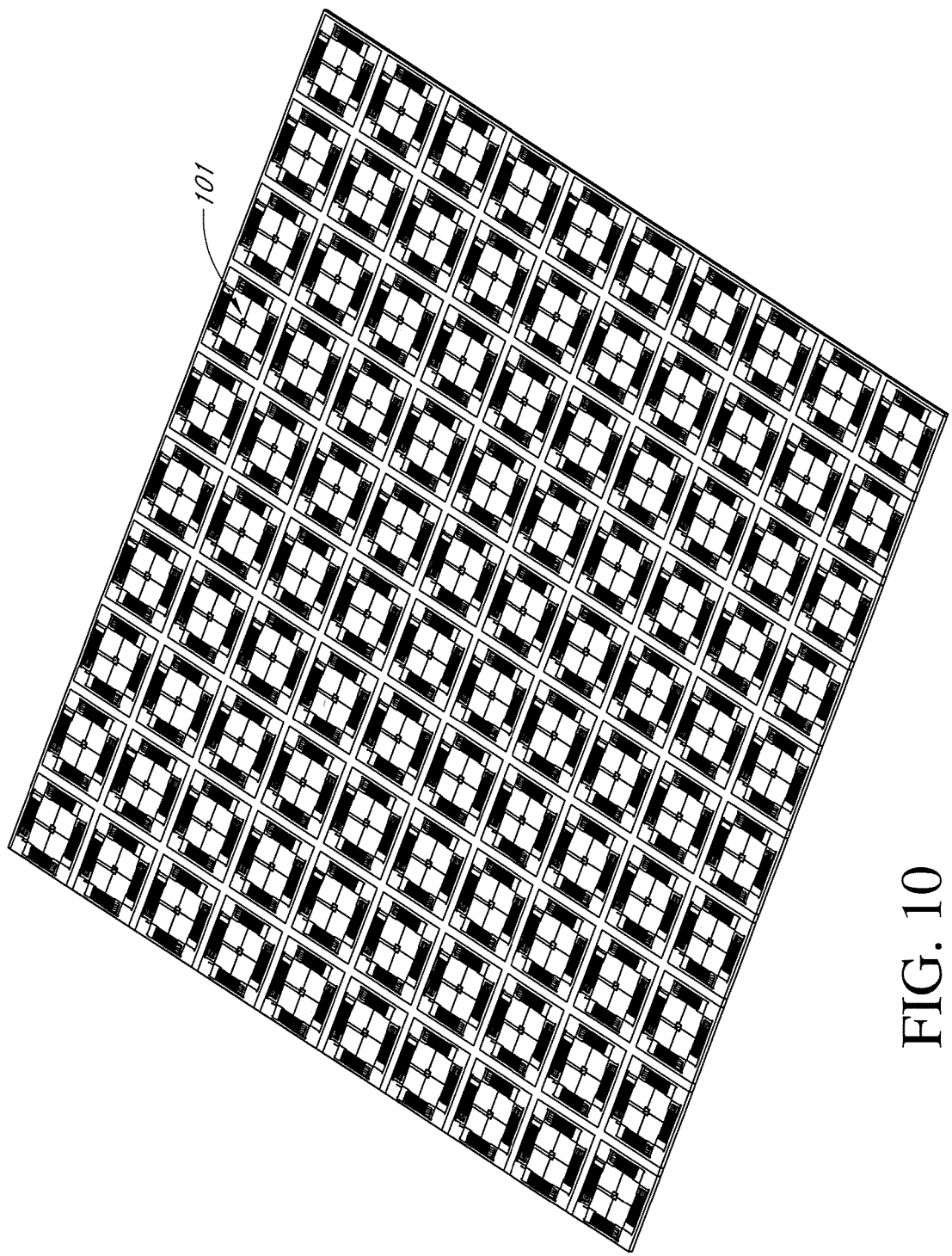
FIG. 10 depicts an architecture for an array of single-unit manipulators, in accordance with various embodiments.

FIG. 10 illustrates an architecture for packing single-unit manipulators 101 onto a wafer, in accordance with various embodiments, the features of which can be used as illustrated or in combination with other embodiments disclosed herein.

Figure 11:
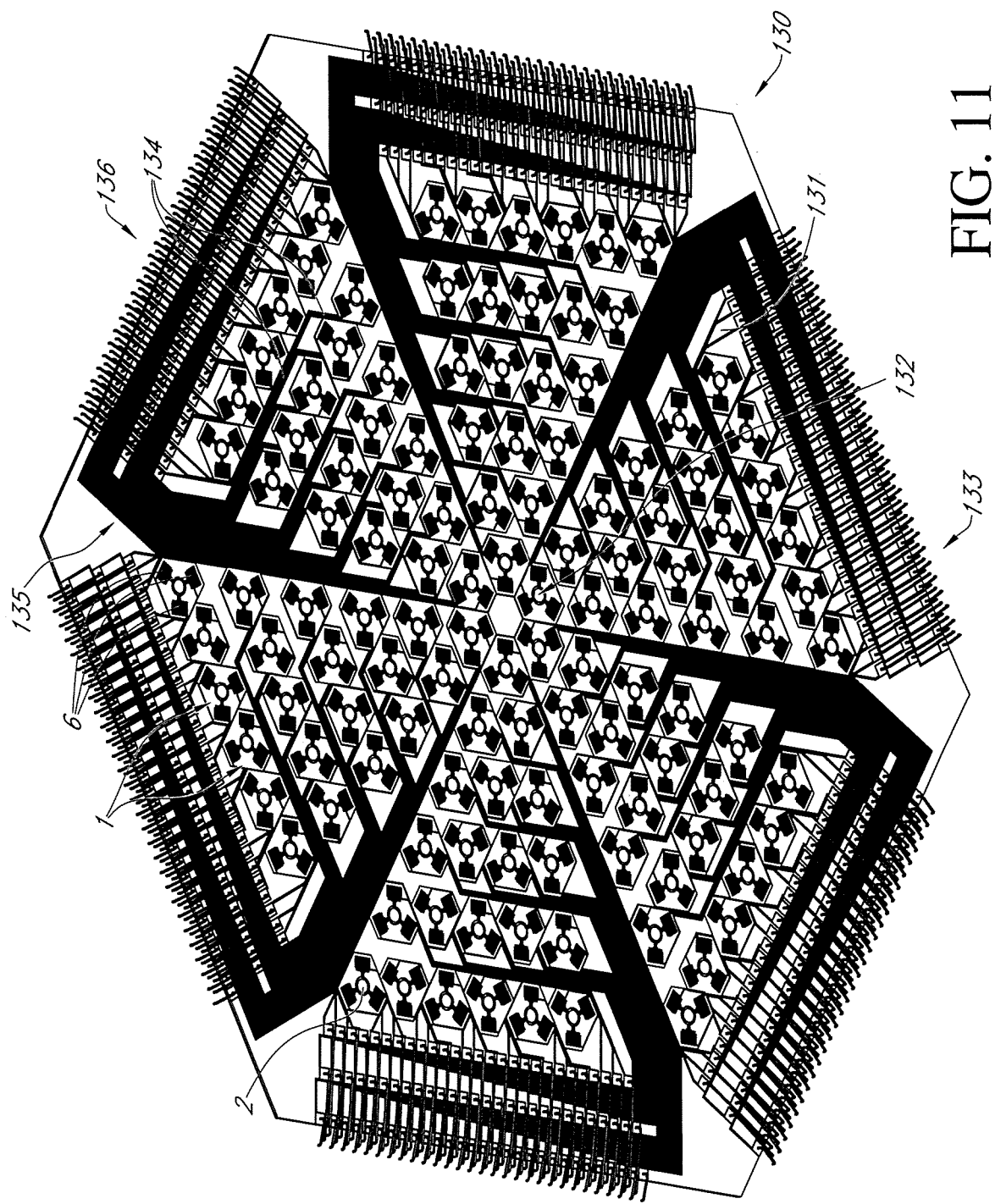
FIG. 11 illustrates a multiple-needle manipulator including an array of single-unit actuators, in accordance with various embodiments.

FIG. 11 illustrates a manipulator array 130 (or multiple-needle manipulator 130), in accordance with various embodiments, the features of which can be used as illustrated or in combination with other embodiments disclosed herein. The multiple-needle manipulator 130 can include a parallel array of single-unit manipulators 1 as illustrated, for example, in FIG. 1. As described, each single-unit manipulator 1 can have a stage 2 and three actuators 6 can be positioned to provide a force in a different direction to the stage 2. The actuators 6 can be arranged, for example, at 120° intervals about the stage 2. Also as shown, each single-unit manipulator 1 can have a minimum footprint shape dictated by the actuators 6.

FIG. 11 further shows a number of single-unit actuators 1 arranged, or 'packed', into sub-arrays 131 which form a parallel-array 132 of the multiple-needle manipulator 130.

Figure 12:
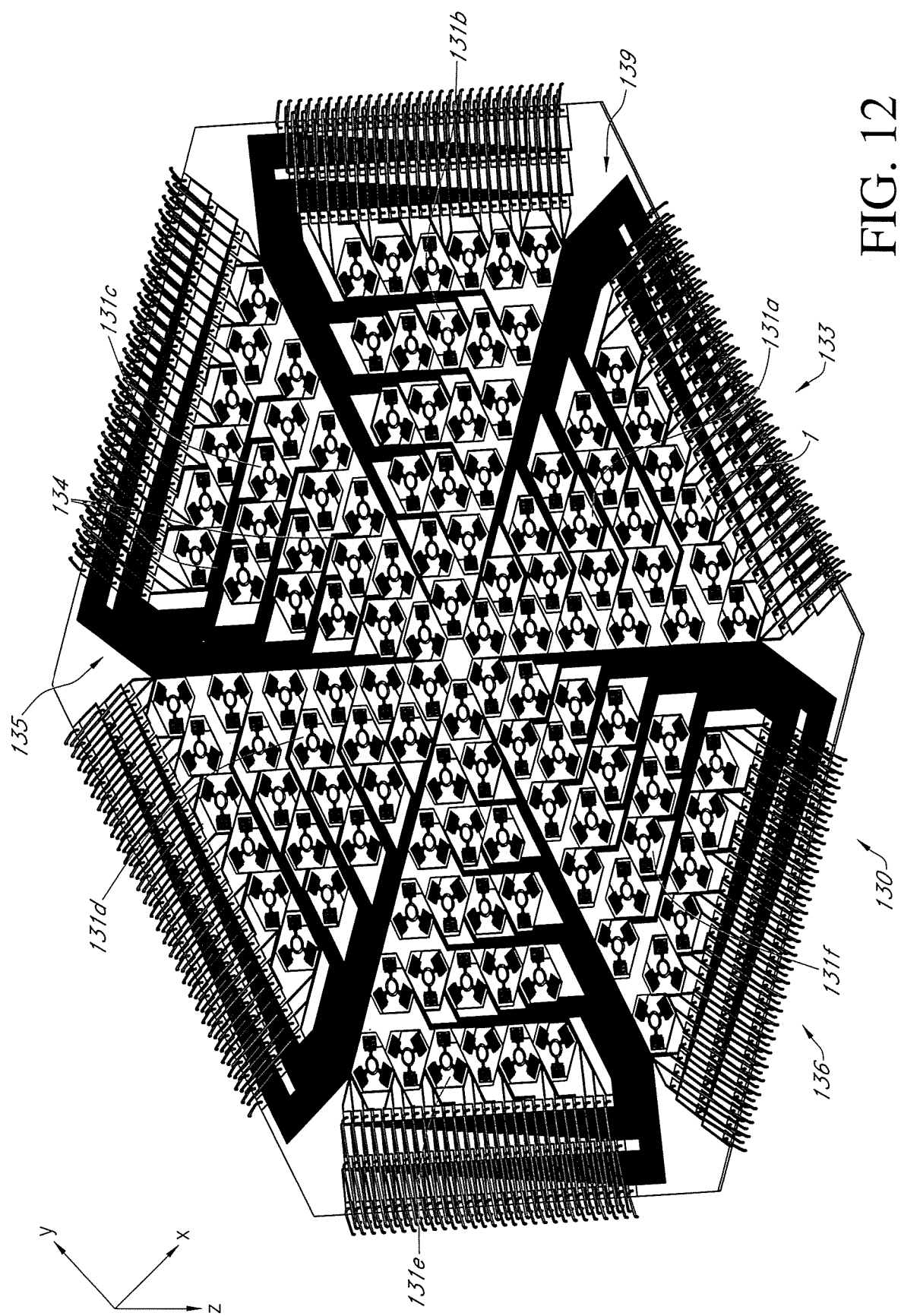
FIG. 12 illustrates an interconnect provided by the periphery of the multiple-needle manipulator of FIG. 11.

FIG. 12 shows six sub-arrays 131a to 131f. Each sub-array 131 has an interconnect 133 for the single-unit manipulators 1. The interconnect 133 allows connection of a voltage source to provide an electrostatic field within each comb-drive 11 to activate each actuator 6 (see, for example, FIGS. 1-4). The interconnect 133 can allow for individual actuation of each actuator 6 of each single-unit manipulator 1. The interconnect 133 shown in FIG. 11 has three rows 134 (also referred to as local interconnect), 135 (also referred to as transitional interconnect) and 136 (also referred to as universal interconnect) of connections. These interconnects are metallic wires commonly fabricated out of Copper (Cu) or Aluminium (Au) that forms the three rows connecting the different parts of the single-unit manipulators to the external circuit. The support beams 8 holding the fixed comb-fingers on each of three sides A, B and C (refer back to FIG. 1) have their individual interconnects each at a single applied potential while the support beams 8 holding the free comb-fingers on each of the three sides A, B and C have a single interconnect at a single potential that also charges the stage 2. The tower 4 has a separate interconnect at a different potential. Therefore every single-unit manipulator can have, for example, five interconnections, leading to an array of such actuators all resulting in different rows 134, 135 and 136 of interconnections in order to avoid wire collision when connecting to an external circuit. Also as shown in FIG. 11, the interconnect 133 is provided via universal interconnect 136 of each sub-array 131.

The arrangement of multiple-needle manipulator 130 can be determined by analysis of the layout such as interconnect routing, floor planning of the placement of single-unit manipulators 1. The arrangement can include considerations distinct from the case of high-performance IC circuit technologies such as from Intel™ and AMD™. In these technologies, factors such as interconnect parasitic impedances, power dissipation, noise, bandwidth, transistor gate delays and loads are critical with an interconnect density of 1-4 million per square centimetres. The density of the interconnections of the interconnect 133 can be orders of magnitude lower than for IC technologies due to the significant size of the single-unit manipulators 1 ranging in a few millimetres such as, for example, 1-6 mm, as compared to transistors of less than 100 nm in size.

A distinction between the use of three-actuator manipulator 1 illustrated in FIG. 1 in a parallel manipulator 130 and the four-actuator manipulator 101 illustrated in FIG. 6 is a reduction in the number of interconnects that would otherwise result in higher power consumption due to a larger capacitance in the interconnect 133. The additional power could result in higher packaging costs and further challenges related to heating. The determination of interconnection capacitance includes the capacitance between the interconnect 133 and the substrate; and the coupling capacitance between neighbouring interconnection rows 134, 135 and 136 or any other neighbouring interconnection rows or wires that may be used.

It is advantageous to reduce noise in voltage levels applied via the interconnect 133. Noise might be induced by coupling capacitance between interconnects and may otherwise cause malfunction in the manipulator 130.

FIG. 12 illustrates an interconnect 133 that can be located, for example, at an edge or periphery of each triangular array 131a to 131f. Each triangular array 131, or functional block, can include an arrangement of single-unit manipulators 1. Each single-unit actuator can be connected via local interconnects 134 that can include lines which extend to transitional interconnects 135 that run through a two-sided periphery 139 of the triangle arrays. These transitional interconnects can be wider and taller than local interconnects 134 provided for each single-unit manipulator 1 in order to provide lower resistance. The transitional interconnects 135 extend to the universal interconnects 136 that provide connections between every functional block and deliver applied voltage from an external power supply to the chip. The transitional interconnects can be the longest in length in the layout of the parallel architecture and are of generally lower resistivity.

For the architecture of the manipulator 130, metallisation for the various interconnects can include of low stress (40-140 MPa) titanium-tungsten (TiW) forming the main adhesion layer and Au as the main conductor. Au can be sputtered or plated to different thickness values to enhance skin depth and conductivity. Cu can be used in place of Au with the advantage of the lower cost. Cu may also have the advantage of being widely used as a standard material for primary interconnection due to its low resistivity. The resistance of a conductor with a rectangular cross-section is given by, $$R = \rho \frac{l}{WH} \quad (1)$$

where $\rho$ is the material resistivity, and l, W, and H are the length, width, and thickness of the interconnect, respectively. The bulk resistivities of Au and Cu are 2.2 $\mu\Omega$-cm and 1.71 $\mu\Omega$-cm, respectively.

As the dimensions of the interconnect wires (not shown) shrink to the order of $\lambda$, the electron mean-free path, the resistivity can increase due to surface and grain boundary scattering. This is because the electrons experience more collisions at the surface, increasing the effective resistivity. In one example, $\lambda$ of copper is 42.1 nm at 0° C. For a one-dimensional surface scattering, the resistivity of a thin wire is given by, $$\rho_s = \frac{\rho_0}{1 - \frac{3(1-p)}{2k} \int_1^\infty \left(\frac{1}{x^3} - \frac{1}{x^5}\right) \frac{1-e^{-kx}}{1-pe^{-kx}} dx} \quad (2)$$

which can be simplified to, $$\rho_s = \frac{\rho_0}{1 - \frac{3(1-p)}{8k}}, k \gg 1 \quad (3)$$

where k=d/λ is the ratio of the thin film thickness to the electron mean-free path, and p is the fraction of the electrons that are elastically scattered at the surface. Considering two-dimensional surface scattering effects in thin wires, the effective resistivity is larger and therefore a reduced k can be used.

Grain boundaries known to the reader act as partially reflecting planes, with grain sizes scaled linearly with wire dimensions. Thus, when the grain size is comparable to λ, the electrons face relatively more grain boundary scattering, thereby further increasing the effective resistivity as is given by this equation, $$\rho_g = \frac{\rho_0}{3\left[\frac{1}{3} - \frac{1}{2}\alpha_g + \alpha_g^2 - \alpha_g^3 \ln\left(1 + \frac{1}{\alpha_g}\right)\right]}, k \gg 1 \quad (4)$$

where, $$\alpha_g = \frac{\lambda p_g}{d_g(1 - p_g)} \quad (5)$$

$d_g$ is the grain diameter, and $p_g$ is the grain boundary reflection coefficient with a value ranging between 0 and 1.

In embodiments which use either Cu or Au as the interconnect material, the resistivity increases linearly with temperature, as given by, $$\rho_t = \rho_0(1 + \beta \Delta T) \quad (6)$$

where β is the temperature coefficient of resistivity and ΔT is the temperature difference with respect to a reference temperature. Since λ decreases with increasing temperature, the k value in Equation (2) becomes larger, thereby leading to a smaller value of. Therefore, β value of a thin wired interconnect is smaller than that of a bulk metal.

Conventional interconnects, such as used in IC chips, can generally be designed based on fast transmission of signals between the transistors, and generally use design tree models such as A-tree, P-tree, H-tree, X-tree and C-tree to minimize the wire length of the interconnects. Unlike on-chip interconnect models (single and parallel coupled) for integrated circuits (ICs) dominated by gates, which can include complicated layouts such as lumped C/RC/RLC models to distributed transmission lines configured all orthogonal to each other, the relatively simpler layout of the parallel-manipulator 130 includes non-orthogonal wiring connections. This wiring connection orientation is due, at least in part, to the relative arrangement of the manipulators 1 and their actuators 6. The architecture of parallel-manipulator 130 can include a plurality of single-unit manipulators 1, each with a plurality of actuators 6 (for example, three) arranged into triangle arrays 131, which can be arranged in a hexagon with interconnects 133 at the periphery of the hexagon. This architecture minimizes the distance of lines from interconnects 133 to actuators 6 yet maximises the density of single-unit manipulators 1 in a given surface area available on a chip. The architecture illustrated in FIG. 12, which may be described as having triangular-island structures in the physical layout of the array, takes advantage of splitting the interconnect into smaller segments such as local 134, transitional 135 and universal 136 to reduce any signal delay occurring in the various interconnects.

By way of illustration a comparison to a circular or rectangular or square layout for the parallel architecture is considered. A corner-to-corner interconnect length would be significantly longer in these architectures. In IC chips, the delay of an RC interconnect is $0.377RCl^2$, where l is the wire length. Therefore, repeaters can be introduced to reduce interconnect delay by splitting the interconnect into k segments, thereby reducing the interconnect delay term to $0.377RCl^2/k$. Using similar conceptualisation that the sum of section interconnect delays caused by such repeater insertion is smaller than the delay in original longer interconnect path, choosing, for example, a hexagonal parallel architecture interconnect design layout, can succeed in splitting an otherwise long interconnection pathway into smaller segments using the arrangement of the manipulators as discussed herein. FIG. 12 illustrates a universal interconnect 136 in the array 130. The universal interconnect receives control voltages to activate the actuators 6 and the parallel plate actuator formed between stages 2 and towers 4. The voltages control the manipulators 1.

Figure 26:
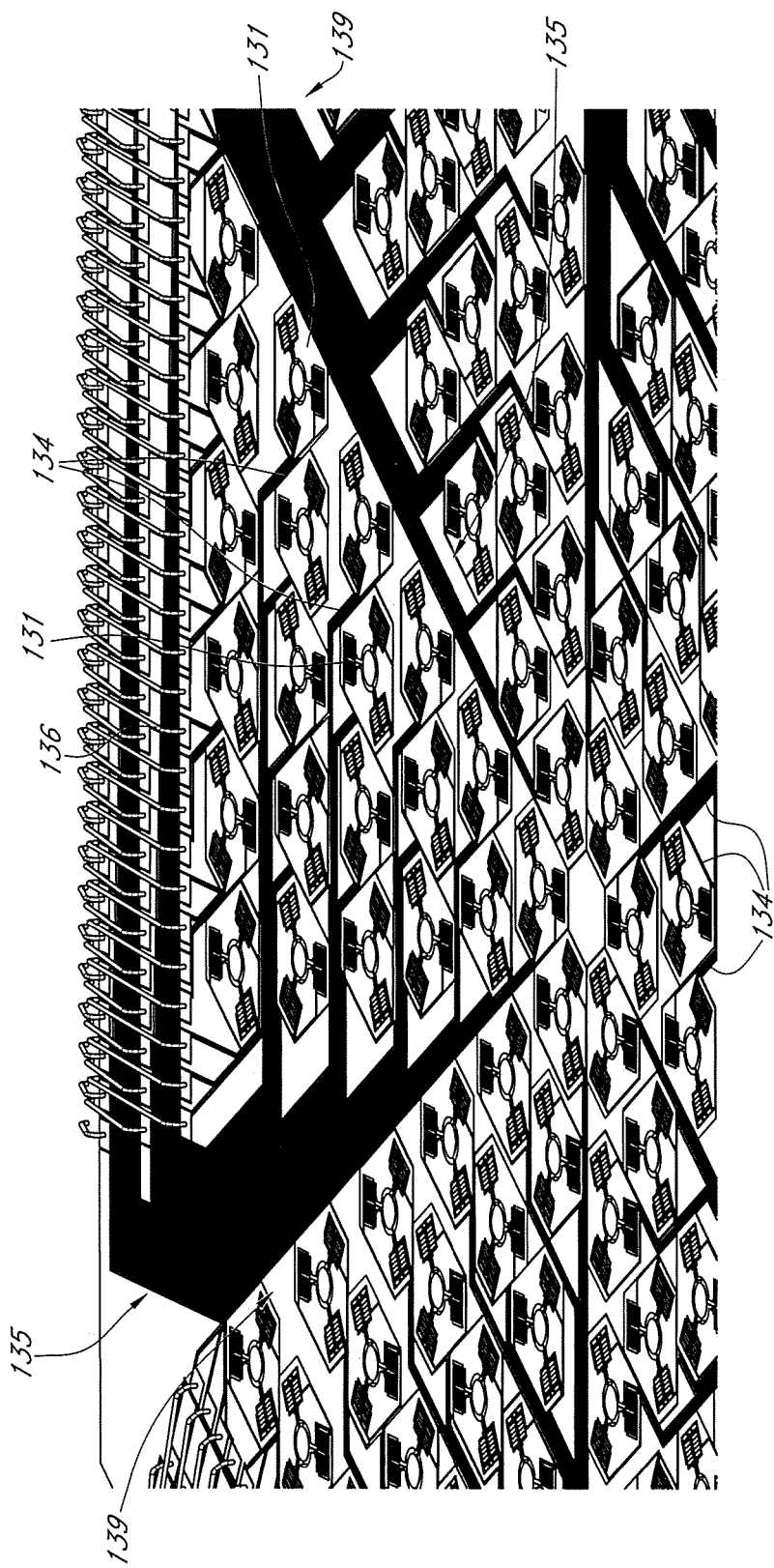
FIG. 26 illustrates an array including an arrangement of interconnects, in accordance with various embodiments.
Figure 27:
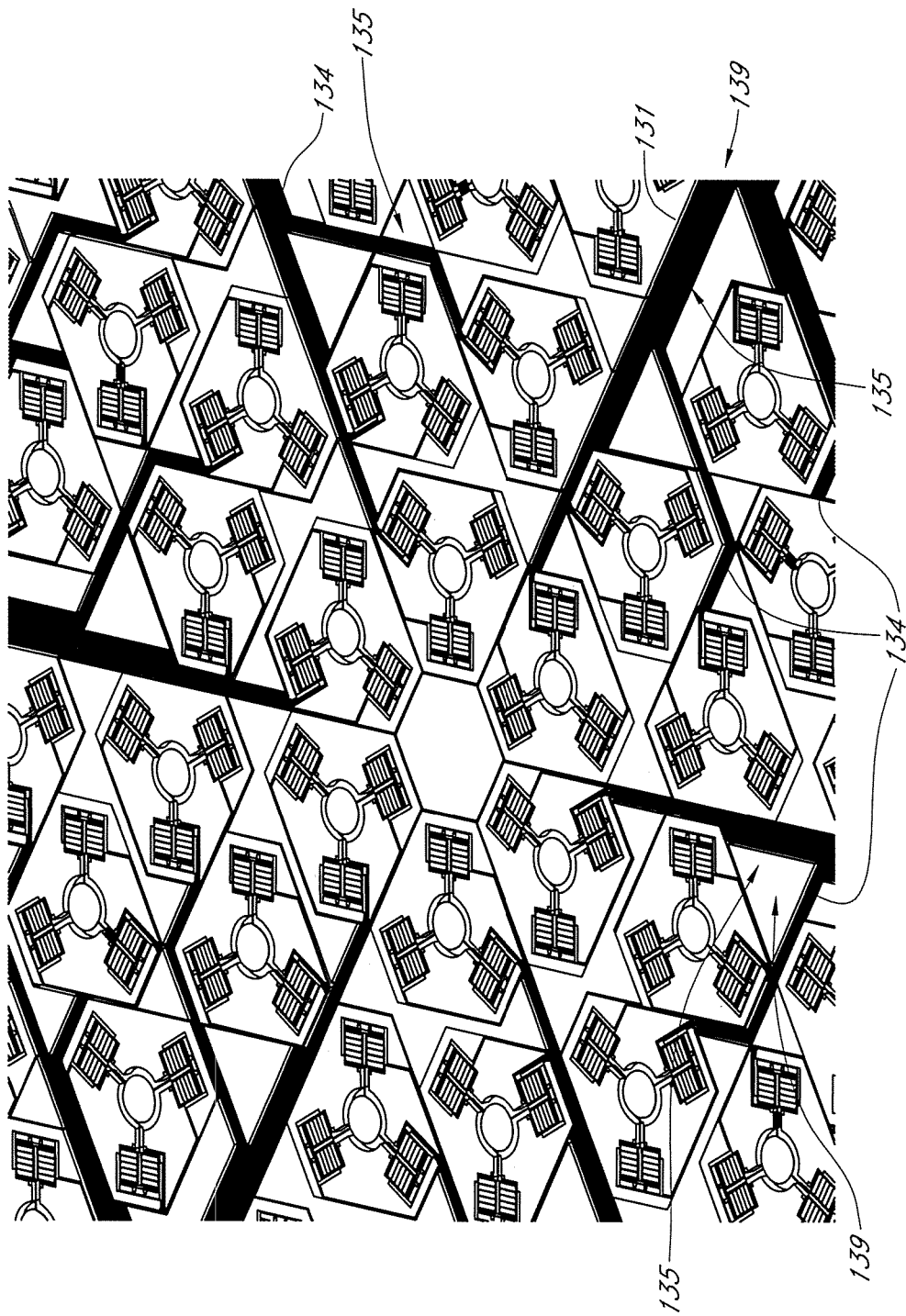
FIG. 27 illustrates an array including an arrangement of interconnects, in accordance with various embodiments.

FIGS. 26 and 27 illustrate interconnections between the universal interconnects of FIG. 12 and the single-unit manipulators 1, in accordance with various embodiments, the features of which can be used as illustrated or in combination with other embodiments disclosed herein. In FIG. 27, transitional interconnects 135 located at a side periphery of the triangle formed by an array 131 connect to universal interconnects 136. The transitional interconnects 135 form step-wise wedge-shaped regions in the sub-array 131. Local interconnects 134 connect between transitional interconnects 135 and single-unit manipulators 1. The local interconnects form step-wise wedge-shaped regions in the sub-array 131.

Figure 13:
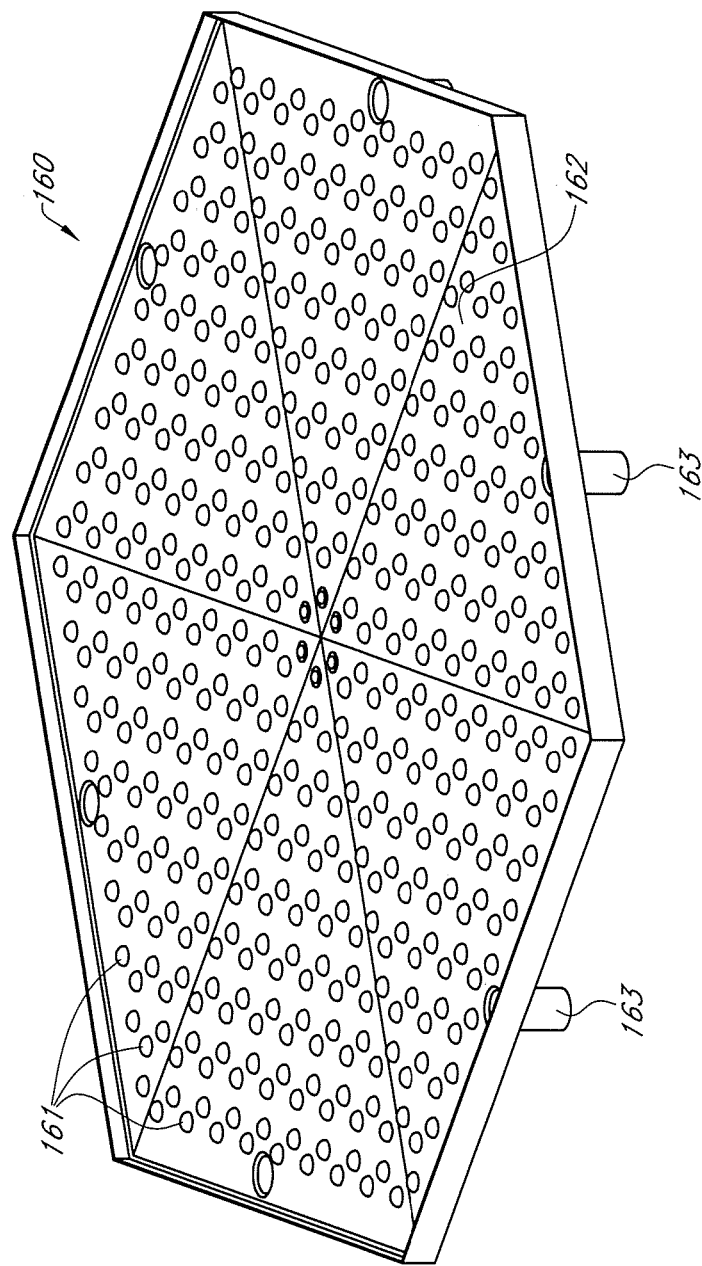
FIG. 13 illustrates a device with a single-unit actuator array in alignment with an array of cell-traps, in accordance with various embodiments.
Figure 30:
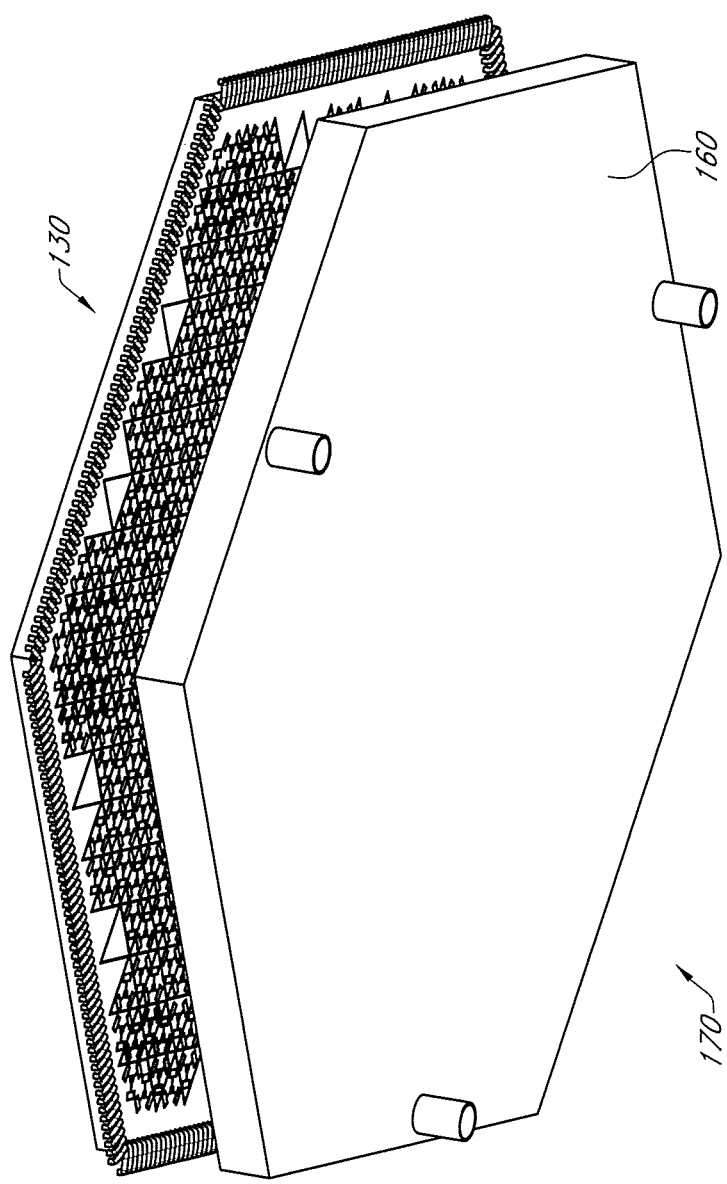
FIG. 30 illustrates a device including a cell trap and parallel-manipulator, in accordance with various embodiments.

FIG. 30 illustrates a device 170, which can be a cell injection device, which can include a cell trap 160 used in conjunction with the parallel-manipulator 130 to trap cells and locate individual cells in spatial communication with a respective single-unit manipulator 1. The single-unit manipulators could then be used, for example, for injection by needles 3 manipulated by stages 2, in accordance with various embodiments, the features of which can be used as illustrated or in combination with other embodiments disclosed herein. The cell trap 160 can be formed from a substrate made from, for example, a glass, a semiconducting material, a metal, a polymer, a composite, a nanostructured material, a crystalline material, or a combination thereof. FIG. 13 illustrates the cell trap 160 configured to capture a plurality of cells, for example, by holding individual cells 161 in respective micro-chambers 162. The micro-chambers 162 can be arranged with a separation or pitch to match the separation or pitch of the single-unit manipulators 1 in the multiple-manipulator array 130, such that each micro-chamber 162 can be in spatial communication with a respective single-unit manipulator 1. The cells 161 can be added to the cell trap 160 by an input port 163. As stated above, cell trap 160 can be formed on numerous types of substrate materials including, for example, a glass substrate 165.

Figure 14:
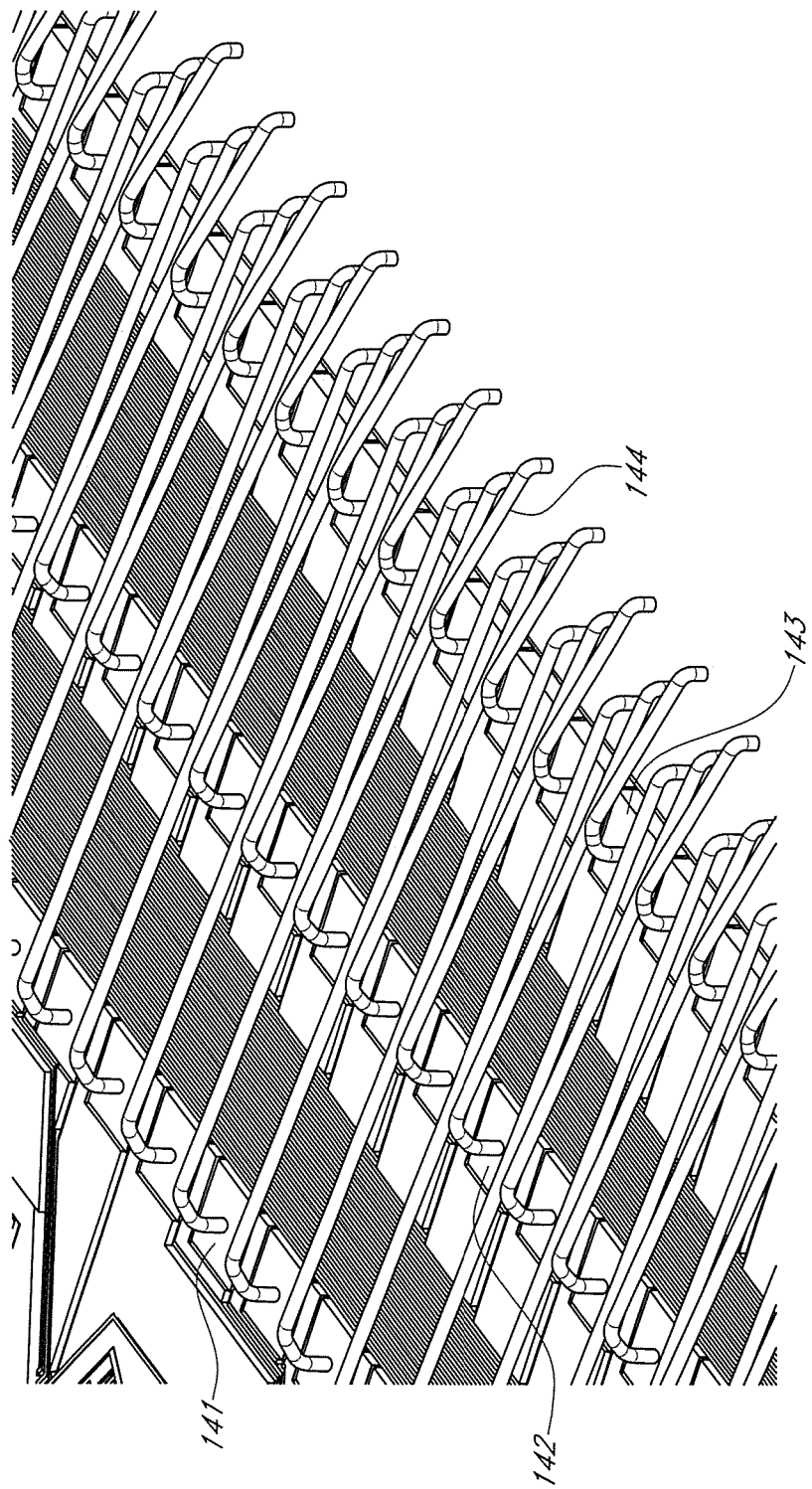
FIG. 14 illustrates wires of an interconnect, in accordance with various embodiments.

FIG. 14 illustrates three rows 141, 142 and 143 of interconnects that are provided for interconnect wires 144.

Figure 15:
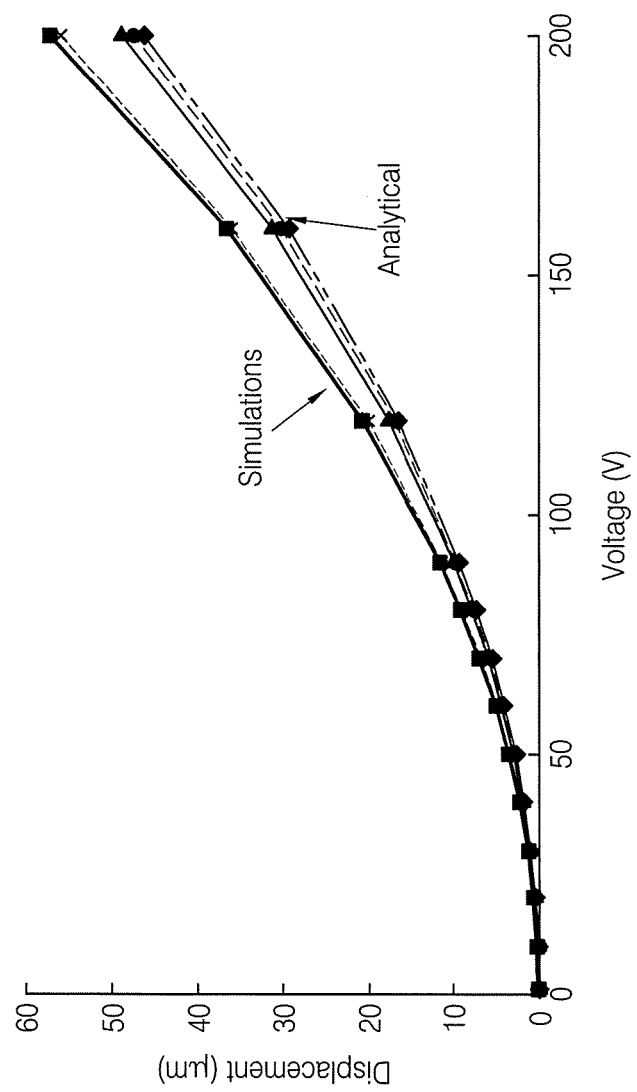
FIG. 15 illustrates displacement in various axes of an actuation stage included in a single-unit actuator, in accordance with various embodiments.

FIG. 15 illustrates displacement of a stage 2 of the single-unit manipulator 1, in accordance with various embodiments, the features of which can be used as illustrated or in combination with other embodiments disclosed herein. The displacement is shown as displacement caused by given tethers 5. Both simulated (solid line) and analytical (dotted line) displacements are depicted.

Figure 16:
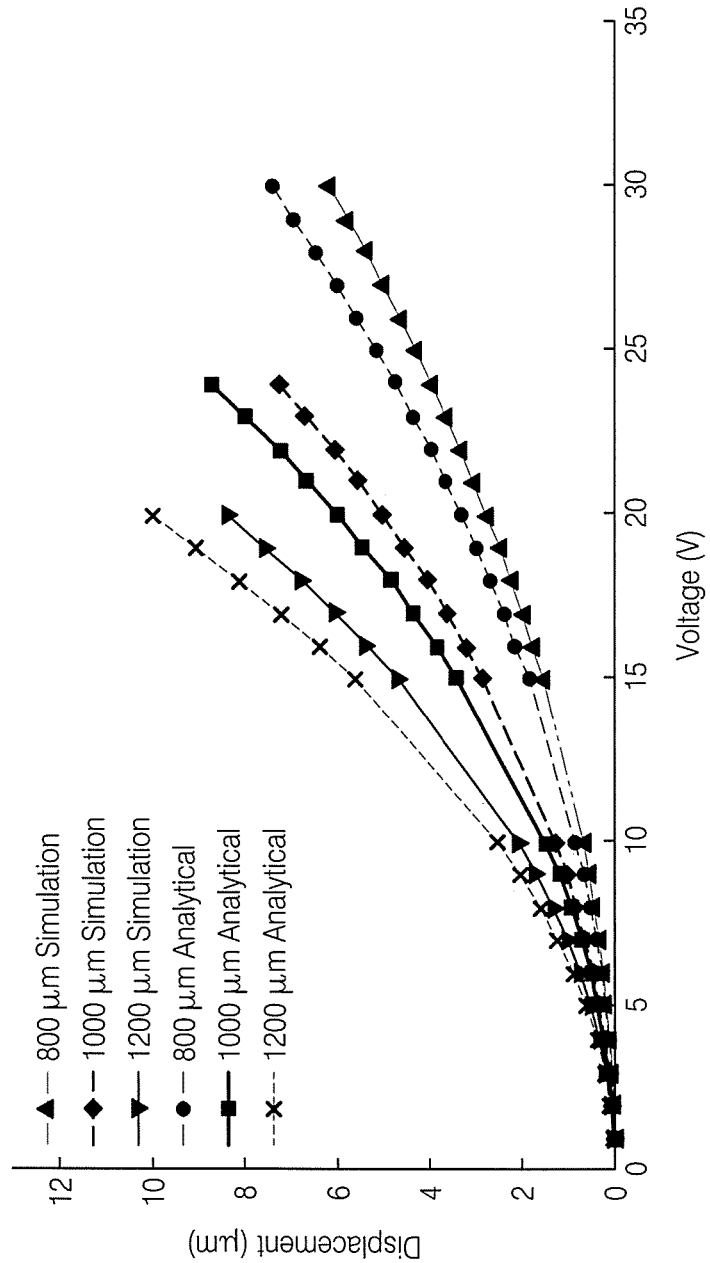
FIG. 16 illustrates displacement in various axes of an actuation stage included in a single-unit actuator, in accordance with various embodiments.

FIG. 16 illustrates displacement of the stage 2 depicted as X-Y displacement or device in-plane displacement and as Z-displacement, or distance from the tower 4 and to the stage 2, in accordance with various embodiments, the features of which can be used as illustrated or in combination with other embodiments disclosed herein. Displacements of the stage 2, such as depicted in FIGS. 15 and 16, can correspond to manipulation via the needle using applied voltages, or electrostatic charges, applied to metal pads (not shown) on actuators 6 to generate forces transferred to the stage 2 via tethers 5 and by voltages, or electrostatic charges, applied to metal pads (not shown) on the towers 4. These voltages, or electrostatic charges, will be the result of voltages applied at interconnects 133 and the effects discussed can occur in parts of the multiple-manipulator 130 such as in the transitional interconnects 135 and local interconnects 134.

For the triangular manipulator, for example, an in-plane X-Y displacement of more than, for example, 36 μm can be achieved at 160 V in one direction in a pull-mode. Thus it can achieve a total in-plane displacement of more than 72 μm (±36 μm) at 160 V in a pull-pull mode. Neither the tether 5 length nor the thickness of the suspended actuator structure affects the in-plane motion significantly. This is also true if instead of actuating one side, two sides are simultaneously actuated for better targeted control of the microneedle 3. The stretching in the tethers is also negligible in the order of sub nanometres. Nonetheless, in case of the out-of-plane Z motion, the actuation performance is affected more significantly by these parameters. The out-of-plane Z displacement can increase as the length of the tethering beams increase or the thickness of the suspended structure decreases as shown, for example, in FIG. 16. For example, an out-of-plane displacement of more than 6 μm can be achieved at 30 V with a tethering beam length of 800 μm. Since the out-of-plane stiffness of the actuator reduces significantly by such change in dimensions, the same displacement can be achieved at 22 V with a tethering beam length of 1000 μm and at 17 V with a tethering beam length of 1200 μm. It is to be noted that there can be a trade off between the overall surface area of the actuator and its performance. In this case, albeit increasing the length of the tethering beams from 800 μm to 1200 μm does increase the out-of-plane Z motion, it also can increase the surface area of the arrayed actuator by at least 40%. Moreover, increasing the thickness of the suspended structure from 10 μm to 25 μm, for example, can significantly increase the DC voltage required to attain similar out-of-plane Z motion. In this case, it can take approximately 115 V to get a displacement of more than 6 μm. The out-of-plane simulations have been performed for a parallel-plate actuator gap of 15 μm.

Comparing the results of arrays of triangular, single-unit manipulators 1 shown, for example, in FIG. 1 with square, single-unit manipulator 101 shown, for example, in FIG. 6, given all the dimensions being same, several interesting points can be observed. For the in-plane (X-Y) actuation, the displacement achieved with actuation by a single actuator on one side of the plate in a square manipulator 101 may be lesser than that achieved with a triangular manipulator 1. For example, at 160 V, square manipulator 101 can achieve an in-plane (X-Y) motion of around 27 μm with a single side actuated in comparison to slightly above 36 μm with the triangular manipulator 1. Nonetheless, the displacement achieved with square manipulator 101 with actuation by a pair of actuators on either side is slightly greater than that with a triangular manipulator 1. For example, at 160 V, square manipulator can achieve an in-plane (X-Y) motion of around 38 μm with actuation by two actuators compared to slightly above 36 μm with the triangular manipulator Adding an extra actuator does add to the total stiffness of the structure. In terms of out-of-plane actuation, at 30 V, square manipulator achieves a motion of around 4.5 μm compared to more than 6 μm with a triangular manipulator. It becomes evident that a 40% increase in single-unit manipulators, as well as a performance enhancement, can be achieved by reducing an extra side.

Bond metal pads (not shown) used in single-unit manipulators 1 and multiple-needle manipulator 130 provide electrodes for electrostatic charge applied separately to the fixed comb-fingers 15, moving comb-fingers 14 which provide in-plane (X-Y) actuation and the stage 2 and tower 4 which provides vertical micro-stage manipulation for the stage 2 and needle 3. The pads can be formed of a thin layer of Titanium-Tungsten and gold (~850 A) with low film stress. They can be fabricated, for example, by blanket physical deposition of the metal film followed by wet chemical etching and patterning. The pads can sit on a silicon oxide insulating layer (not shown). The metal pads (not shown) can be wire bonded to the printed circuit board and external electronics at the interconnect 133.

The multiple-needle manipulator 130 can be formed of a silicon-on-insulator wafer (not shown). This is a sandwich structure including a device layer (active layer) on top, a buried oxide layer (insulating $SiO_2$ layer) in the middle (e.g., a few microns in thickness), and a handle wafer (bulk silicon) in the bottom. Such isolation of the device layer from the bulk silicon layer results in lower parasitic capacitance can significantly improve the performance and reduce the power consumption of integrated circuits. The bottom substrate can be a standard silicon wafer several hundred times the thickness of the buried oxide layer.

The tower 4 can be a tower shaped electrode (made of, for example, silicon) located under the central stage 2. Tower 4 provides an electrostatic, or capacitive, force for the stage 2, thereby resulting in deflections of the tethers and spring flexure beams 9. The tower top surface area (not indicated) can be greater than the surface area of the stage 2 by a factor of, for example, two to three in order to have significant surface area still available to produce attractive electrostatic force after in-plane (X-Y) motion caused by the actuators 6 makes the location of the needle 3 ready for out-of-plane (Z) motion. The cross-section (not indicated) of the tower 4 can be circular due to the circular geometry of the micro-stage, with enough access area on each side for larger displacements, in comparison to other geometries. The movement described here in reference to X, Y and Z axes may be referred to as manipulation as it is used to manipulate the needle 3 for injecting a cell for example.

The needle 3 may be referred to as a microneedle or nanoneedle. The needle 3 can be assembled onto the micro-stage or stage 2, which is circular in shape, in order to provide geometric symmetry for the particular three-sided manipulator 1. Since an attractive capacitive force between the stage 2 and the bottom tower (e.g., silicon tower) or tower 4 is proportional to the surface area, a larger area of the top or cross-section of the tower 4 will result in larger capacitance. Thereby, a larger vertical force for penetration through the cell membrane will be generated in the Z-axis. Nonetheless, there can be a proportional relationship between increasing the surface area of the micro-stage and achieving an optimum surface area of the actuator, critical for the parallel architecture.

Figure 17:
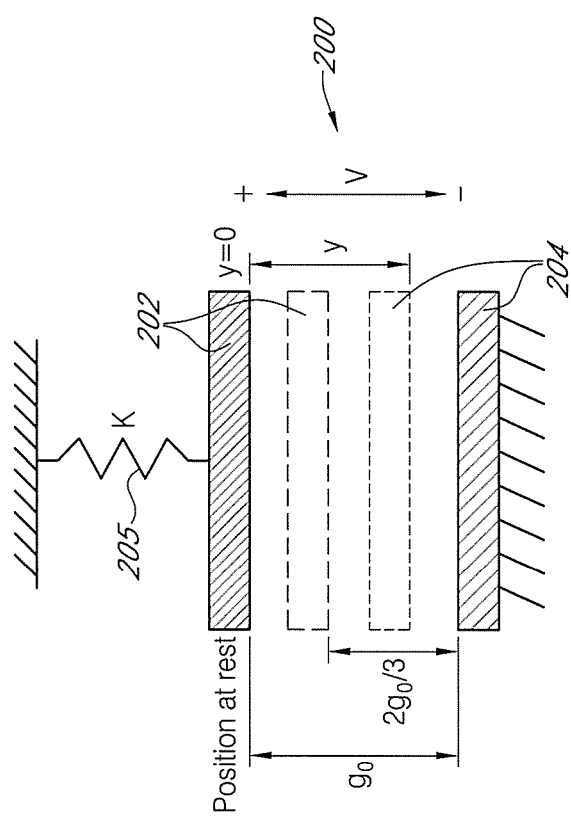
FIG. 17 schematically depicts a parallel plate actuator illustrating an operating principle in accordance with various embodiments.

FIG. 17 illustrates a single-unit manipulator as a system 200 comprising a stage 202 which is acted upon in the Z-axis by electrostatic attraction with a tower 204 and a restoring bias 205 or spring with spring constant k, in accordance with various embodiments, the features of which can be used as illustrated or in combination with other embodiments disclosed herein. The bias 205 in this system is the combined effect of tethers 5, which experience strain, and spring flexure beams 9. In some examples, forces on the stage may also be biased, actuated or both in part by actuators 6. Actuation of the stage 2 can involve balancing forces applied by the actuators 6 and tower 4, which can be controlled by voltages applied at interconnects 133 and forces applied by spring flexure beams 9 and tethers 5.

Figure 18:
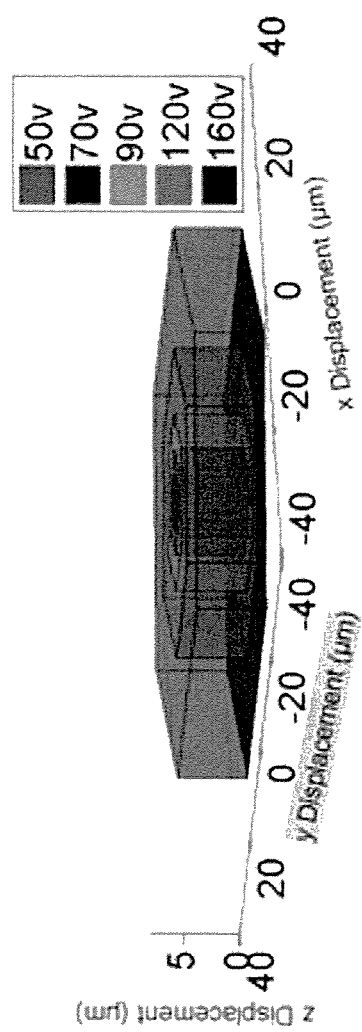
FIG. 18 illustrates a simulation of actuation of a single-unit manipulator, in accordance with various embodiments.
Figure 19:
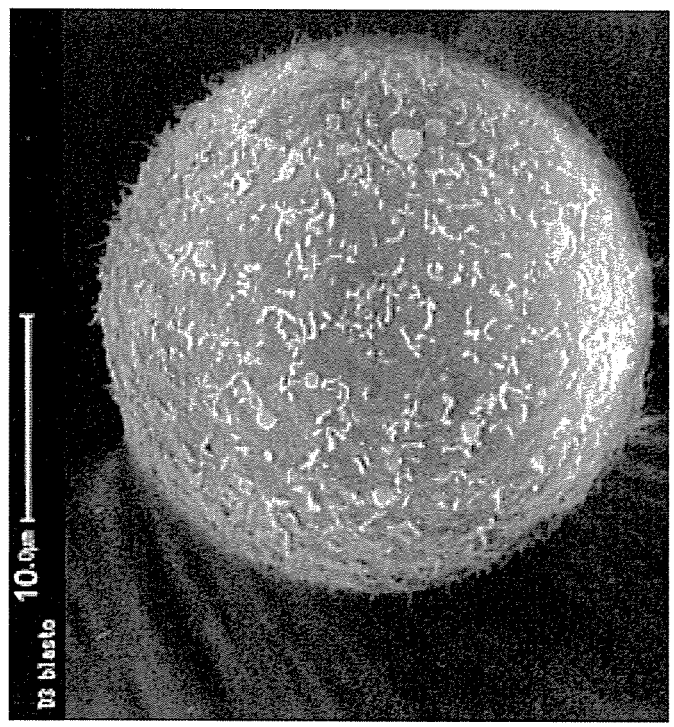
FIG. 19 is a picture of a biological cell which has been injected, in accordance with various embodiments.

For the in-plane motion, the displacement achieved with one actuator functioning in a single-unit manipulator with four actuators can be less than that achieved with a single-unit manipulator with three actuators. For example, at 160 V, a single-unit manipulator with four actuators can achieve an in-plane motion of around 27 µm with a single actuator functioning in comparison to slightly above 36 µm with a single-unit manipulator with three actuators. Nonetheless, the displacement achieved with a single-unit manipulator with four actuators with two actuators functioning is slightly greater than that with a single-unit manipulator with three actuators design. For example, at 160 V, a single-unit manipulator with four actuators can achieve an in-plane motion of around 38 µm with two actuators functioning compared to slightly above 36 µm with the single-unit manipulator with three actuators. Adding an extra side (or actuator) does add to the total stiffness of the structure. In terms of out-of-plane actuation, at 30 V, a single-unit manipulator with four actuators achieves a motion of around 4.5 µm compared to more than 6 µm with a single-unit manipulator with three actuators. It becomes evident the performance enhancement in actuation by reducing an extra side while increasing the number of three-actuator single-unit manipulators up to 40% (compared to four-actuator single-unit manipulators) that can be integrated in the parallel architecture surface area. The zone of actuation is shown through a 3D volume plot in FIG. 18 with respect to a human cell type in FIG. 19. FIG. 18, in particular, illustrates displacement of the stage 2 in X, Y and Z axes with various voltages displayed applied at the interconnect 133, in accordance with various embodiments, the features of which can be used as illustrated or in combination with other embodiments disclosed herein. FIG. 19, in particular, shows a biological cell such as one might be injected by a needle 3 and associated manipulator 1 according to various embodiments of the present invention. This actuator has a tethering beam length of 800 µm, a suspended structure thickness of 10 µm and an actuator gap of 15 µm. Given the cell size is about 25 µm in diameter, the actuator can easily move the nanoneedle over the size of the cell both in-plane and to a reasonable extent in out-of-plane.

Further detail on the role of the tethers and spring-flexure beams 9 will now be given in reference to FIGS. 20 to 24.

Figure 20:
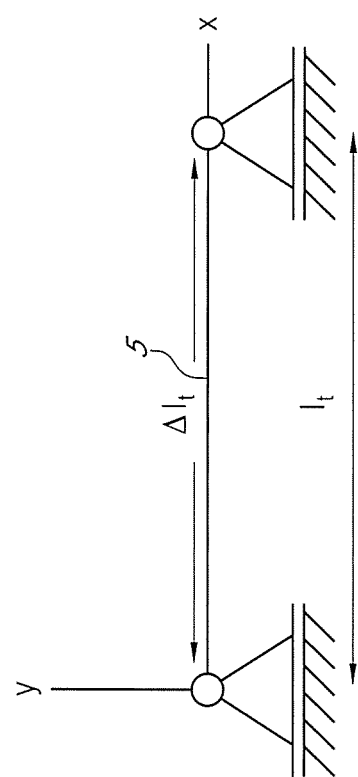
FIG. 20 schematically illustrates a mechanical system a representing single-unit manipulator for the purpose of stiffness modelling, in accordance with various embodiments.

FIG. 20 illustrates for reference a tether 5 as a simple mechanical system for the purpose of analysis, in accordance with various embodiments, the features of which can be used as illustrated or in combination with other embodiments disclosed herein.

Figure 21B:
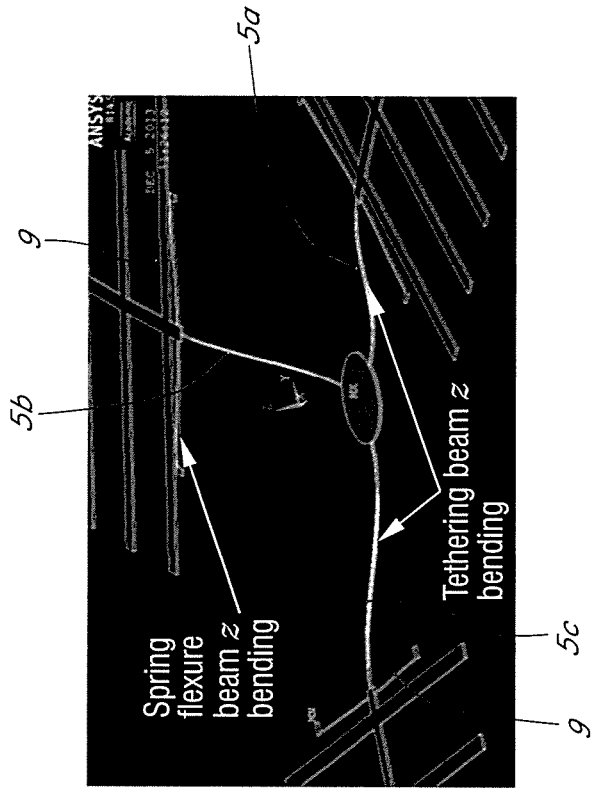
FIGS. 21a and 21b schematically illustrate a tether under longitudinal stress and experiencing longitudinal strain for the purposes of analysis, in accordance with various embodiments.
Figure 21A:
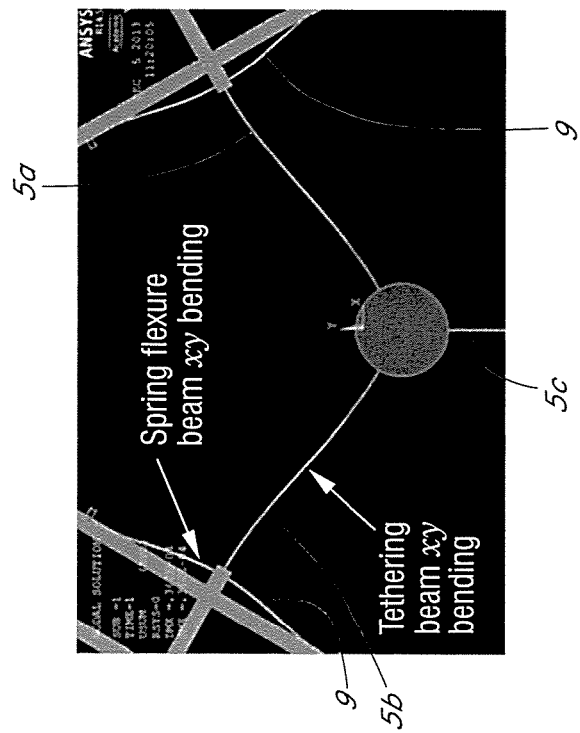

FIGS. 21a and 21b illustrate, for reference below, bending tether 5 and corresponding flexure of spring flexure beams 9, in accordance with various embodiments, the features of which can be used as illustrated or in combination with other embodiments disclosed herein.

When tether 5c experiences a pull motion due to the electrostatic force of the comb drive actuators, tethers 5a and 5b experience bending in that results in the bending of the spring flexure beams. Similarly, when the parallel plate actuator experiences an electrostatic force in the vertical direction, the central stage 2 actuates downwards or upwards and therefore the tethers 5a, 5b and 5c experiences corresponding bending in the Z axis.

Assume, for example, a single-unit manipulator with three actuators of suspended structure thickness of 10 µm, an increasing parallel-plate actuator gap, and all the other dimensions are kept constant. Applying the above concepts, increasing the parallel-plate actuator gap from, for example, 15 µm to 30 µm and 50 µm, can affect the out-of-plane motion significantly. Comparing the results for tethering beam length of 800 µm, it takes more than 200 V to achieve an out-of-plane motion of more than 6 µm with a gap of 30 µm and around 320 V with a gap of 50 µm. Increasing the length of the tethering beam may lessen the requirement of voltage, but it can affect the surface area of the arrayed architecture. Albeit decreasing the actuator gap does result in greater out-of-plane motion at a low voltage, it can limit the total motion range of the actuator due to the pull-in effect as shown in FIG. 17.

The maximum bending and stretching of the tethers 5 and spring flexure beams 9 due to translational and axial deflections can be critical for actuator performance. The motion performance of these beams can be dependent on the effects discussed below.

A first effect is minimum longitudinal stretching of tether 5, shown schematically in the mechanical system of FIG. 20.

A second effect is maximum bending of tethers for 3D (X, Y and Z) motion range with decoupled motion across the axes. Motion coupling is a parasitic behaviour that significantly affects the motion performance and structural integrity of the actuator.

Under loading, bending of the tethers becomes a primary critical behaviour that should generally occur with minimum coupling across the axes, as shown in FIG. 16.

A third effect is the relationship between bending of spring flexure beams 9 and bending of tethers 5, as shown in FIG. 16.

Two of the many important attributes that govern the behaviour of the actuator are bending and longitudinal stretching. Knowledge of stretching of the tethers 5 assists in understanding the fatigue performance under repeated loading of the beams. Stretching can lead to increasing stiffness of the tethers which can affect the overall strength of the structure formed of the stage 2 and tethers 5. The fatigue life of the beams under cyclic loading can be significantly affected with stretching in the tethers 5. Moreover with increasing bending in the beams, plastic behaviour can be induced in these suspended beam structures. This can result in a permanent elongation of the tethers and thus affecting the accuracy of motion performance.

Knowledge of bending of the tethering and spring flexure beams 9 allows a trade-off between the desirable maximum bending of these beams and the permissible dimensions. For example, increasing the length or decreasing the thickness of the beams will apparently increase the motion performance, but possibly at the cost of total size of the actuator and spring stiffness of the actuator. Size of the actuator can have an impact on the density or pitch of manipulators 1 on a multiple-needle manipulator 130. The 3D behaviour of the spring flexure beams 9, which provides restoring force, can depend on the performance of the tethers 5. The stretching and bending phenomena can be investigated for many different parameters including, for example, the following parameters, due to their significant contribution toward the motion of the actuator: cross-section area (w×h), aspect ratio (w/h) and length (l) of the tether 5 or beam 9. Three thicknesses 10 µm, 20 µm and 25 µm were used to study the beam behaviours as limiting parameters. The interference in deflection of the tethers 5 and spring flexure beams 9 for both in-plane and out-of-plane actuation were taken into account. Based on these criteria and parameters, six such scenarios were mapped out and analysed to conceptualise suitable beam dimensions. The result of this analysis was that the cross-section area of the beams should not be greater than, for example, 50 μm², and the aspect ratio not greater than, for example, 0.5, for optimal trade-off between bending and integration of multiple actuators in a parallel architecture. Longitudinal stretching is found to be negligible, several orders of magnitude lower than the 3D bending of the beams. Such design conceptualization and analysis provides critical information in terms of cross-section area and aspect ration of the beams for optimal trade-off between bending and integration of multiple actuators in a parallel architecture.

Another effect is in-plane stretching of tether 5 compared with its bending. As discussed above, minimising the tether 5 stretching is ideal.

Another effect is in-plane, X-Y, bending of spring flexure beam 9 compared with bending of tethers 5, as shown in FIG. 21.

Another effect is out-of-plane, Z, bending of spring flexure beam compared with bending of tether, as shown in FIG. 21.

A further effect is in-plane bending of tethers 5 compared with their out-of-plane bending.

Another effect is in-plane, X-Y, bending of spring flexure beam 9 compared with its out-of-plane bending.

A further effect is stretching and bending of tethers 5 and spring flexure beam compared with length.

Figure 22A:
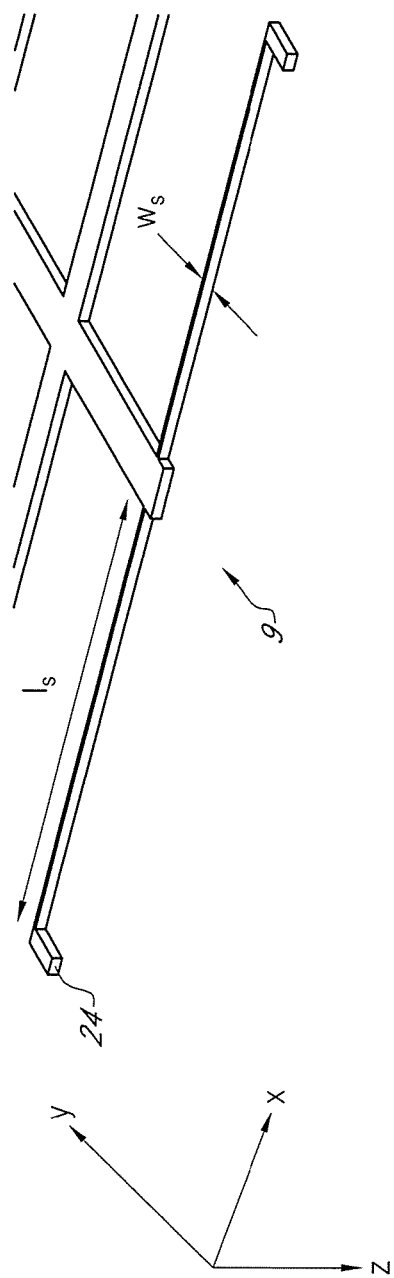
FIGS. 22a to 22c illustrate spring flexure beams, in accordance with various embodiments.
Figure 22B:
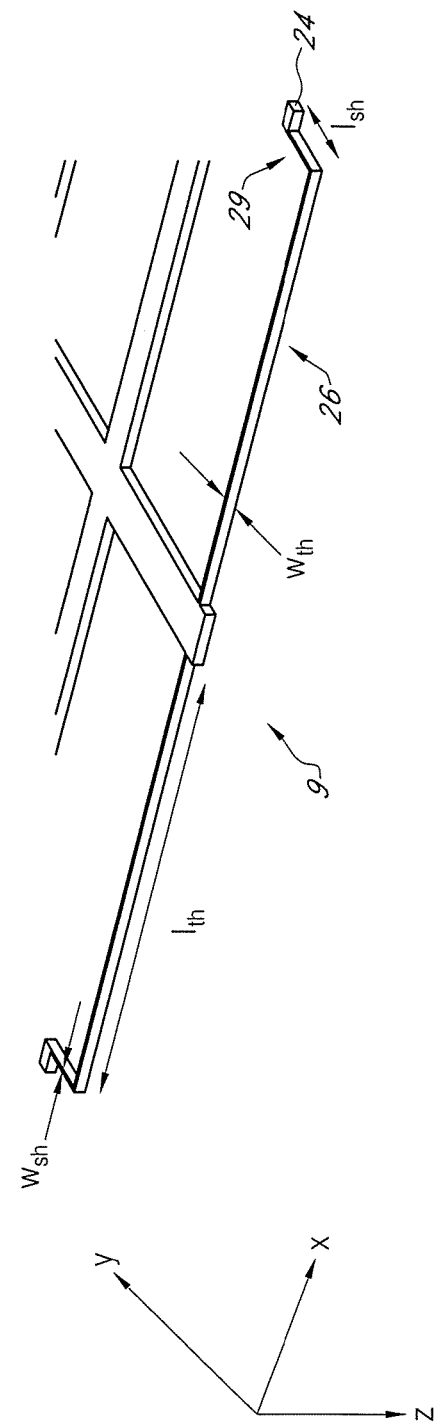
Figure 22C:
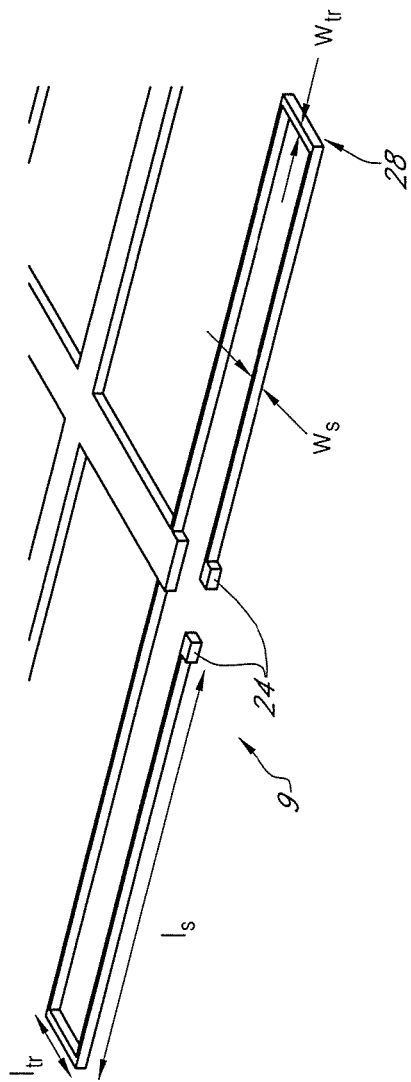

FIGS. 22a to 22c illustrate three types of spring flexure beam 9 which may be used in accordance with various embodiments, the features of which can be used as illustrated or in combination with other embodiments disclosed herein. FIG. 22a illustrates the type which may be referred to as clamped-clamped. FIG. 22b illustrates a type which may be referred to as crab leg. FIG. 22c illustrates a type of spring flexure beam 9 which may be described as single folded.

The following provides further analysis of the bending and flexing of the tethers 5 and the above-described three types of spring flexure beams 9.

The longitudinal stretching of the tether 5 is computed by, $$\Delta l_t = \frac{F_e l_t}{EA} \quad (7)$$

where $F_e$ is the electrostatic force, $l_t$ is the lengths of tether 5, A is the cross-section area of the tether 5 and E is the Young's modulus.

The bending of the tether 5 is computed by, $$w_{max} = \frac{F_e l_t^3}{3EI} \quad (8)$$

where I is the second moment of inertia of the tether 5.
The bending of the spring flexure beam 9 is computed by, $$W_{max} = \frac{F_e l_s^3}{192EI} \quad (9)$$

where $l_s$ is the length of spring flexure beam.

We have investigated the motion performance of the single unit and multiple unit manipulators using finite element analysis (FEA) simulations for three different types of spring flexure beams 9. Namely, clamped-clamped, crab leg and single folded as shown in FIGS. 22a to 22c. The clamped-clamped spring flexure beam of FIG. 22a, with an anchor 24 provided on the ends of beam 9, has a significant stiff nonlinear spring constant due to extensional axial stress in the rectangular beams. When a thigh section 26 is added to the clamped flexure beam (see FIG. 22b), it forms the crab leg spring flexure beam, with an off-center anchor 24 formed via a connecting shin 29. The crab leg spring flexure beam can help reduce stiffness in the undesired direction and extensional axial stress in the flexure. The single folded flexure beam (see FIG. 22c) can also reduce axial stress components in the beams 9 by adding a truss 28 to the parallel arrangement of beams and they are anchored near the center, via anchor 24. This truss 28 allows the end of the flexure to expand or contract in all directions.

For clamped-clamped spring flexure beam 9, the out-of-plane stiffness $K_z$ is, $$K_z = \frac{2Ew_s h_s^3}{l_s^3} \quad (10)$$

For crab-leg spring flexure beam, the axial stiffness $K_{x,y}$ [11] is, $$K_{x,y} = \frac{Eh_s w_{sh}^3 (4l_{sh} + \alpha l_{th})}{l_{sh}^3 (l_{sh} + \alpha l_{th})} \quad (11)$$

Where $h_s$=thickness of the rectangular beam, $l_{sh}$ and $w_{sh}$=length and width of the shin respectively, $l_{th}$ and $w_{th}$=length and width of the thigh respectively and where $\alpha = I_{sh}/I_{th} = (w_{sh}/w_{th})^3$, $I_{th}$ and $I_{sh}$ share the moments of inertia of thigh and shin respectively.

And the lateral stiffness $k_l$ is, $$k_l = \frac{Eh_s w_{th}^3 (l_{sh} + 4\alpha l_{th})}{l_{th}^3 (l_{sh} + \alpha l_{th})} \quad (12)$$

Thus, the stiffness ratio is, $$\frac{K_{x,y}}{k_l} = \frac{w_{th}^3 l_{th}^3}{w_{sh}^3 l_{sh}^3} \left( \frac{4l_{sh} + \alpha l_{th}}{l_{sh} + 4\alpha l_{th}} \right) \quad (13)$$

The out-of-plane stiffness $K_z$ is, $$K_z = \frac{48EI_{x,sh}}{l_{sh}^3} \quad (14)$$

where $I_{x,sh}$=moment of inertia of shin about x-axis.

For single folded spring flexure beam, the axial stiffness $K_{x,y}$ is, $$K_{x,y} = \frac{24EI_{z,s}}{l_s^3} \quad (15)$$

And the lateral stiffness $k_l$ is, $$k_l = \frac{4.8EI_{z,tr}}{l_{tr}^3} \quad (16)$$

The out-of-plane stiffness $K_z$ is, $$K_z = \frac{24EI_{x,s}}{l_s^3} \quad (17)$$

$h_s$=thickness.
where $l_{tr}$=length of the truss and it is assumed that the truss is significantly stiffer than the tethers or beams.

The effect of a lateral pull on the comb drives 6 will now be described.

Apart from the electrostatic force in the x-axis, for example, there is also perpendicular electrostatic force acting along the y-axis, generating a lateral pull on both the movable 14 and fixed fingers 15. Assuming that the movable finger 14 structure moves by a small displacement y along the y-axis, the net electrostatic force $F_{el}$ in the lateral direction generated by both sides of the movable fingers, $$F_{el} = \frac{1}{2}\left[\frac{i\varepsilon t_f(m_o + \delta_x)}{(gs_f - y)^2} - \frac{i\varepsilon t_f(m_o + \delta_x)}{(gs_f + y)^2}\right]V^2 \quad (18)$$

Where $t_f$=thickness of comb fingers 14 and 15, V=actuation voltage and $gs_f$ is the gap spacing between the adjacent comb fingers 14 and 15.
where $\delta_x$ is the comb finger displacement in the x-axis and is given by, $$\delta_x = \pm\frac{F_e}{K_{x,y}} = \pm\frac{1}{2}\frac{i\varepsilon t_f}{gs_f K_{x,y}}V^2 \quad (19)$$

The net lateral electrostatic force $F_{el}$ generated by both sides of the movable fingers, will push them off the equilibrium position instead of pulling them back to the original position, which works like a negative spring. The moving electrode pairs will be unstable without the mechanical restoring force in the y-direction.

The equivalent negative spring constant $k_n$ is, $$k_n = \frac{\partial F_{el}}{\partial y}\bigg|_{y=0} = \frac{2i\varepsilon t_f(m_o + \delta_x)}{gs_f^3}V^2 \quad (20)$$

For stability of the comb-drive actuator 6 without motion being compromised due to lateral deflection, the following relation should generally be satisfied, $$k_l > k_n \quad (21)$$

where $k_l$ is the lateral spring constant.

Substituting Equation (18) in Equation (19), the equivalent negative spring constant as a function of in-plane (X-Y) spring stiffness is, $$k_n = \frac{2K_{x,y}(m_o + \delta_x)\delta_x}{gs_f^2} \quad (22)$$

Thus, from Equations (5) and (6), the maximum static displacement in the direction of motion towards an actuator 6 without motion compromise due to lateral electrostatic deflection, $$\delta_x^{max} = \frac{1}{2}\sqrt{m_o^2 + 2\frac{k_l}{K_{x,y}}gs_f^2} - \frac{m_o}{2} \quad (23)$$

Equation (7) is critical for maintaining the stability of the actuator during in-plane motion. Since the springs on each sides are connected in parallel, the effective in-plane axial spring constant in the direction of motion as derived from the known beam deflection theory is, $$K_{x,y} = 4k_s + k_t = 4\left(\frac{2Eh_s w_s^3}{l_s^3}\right) + \left(\frac{2Eh_t w_t^3}{l_t^3}\right) \quad (24)$$

where $k_s$=in-plane axial stiffness of the spring flexure beam, $k_t$=in-plane axial stiffness of the tethering beam, E=Young's modulus of silicon 129.5 GPa, $h_s$, $w_s$, $l_s$ are the height, width and length of the spring flexure beams respectively, and $h_t$, $w_t$, $l_t$ are height, width and length of the tethering beams respectively.

The effective lateral spring constant perpendicular to the direction of motion is, $$k_l = 4\left(\frac{2Eh_s w_s}{l_s}\right) \quad (25)$$

From Equations (24) and (25), the stiffness ratio between axial and lateral stiffness of the spring and tethering beam system is, $$\frac{K_{x,y}}{k_l} = \frac{4\left(\frac{2Eh_s w_s^3}{l_s^3}\right) + \left(\frac{2Eh_t w_t^3}{l_t^3}\right)}{4\left(\frac{2Eh_s w_s}{l_s}\right)} = \frac{4\left[h_s\left(\frac{w_s}{l_s}\right)^3\right] + \left[h_t\left(\frac{w_t}{l_t}\right)^3\right]}{4\left[h_s\left(\frac{w_s}{l_s}\right)\right]} \quad (26)$$

Thus, the in-plane pull-pull static displacement $U_{x,y}$ is given by, $$F_e = 8F_{act} = \pm K_{x,y} U_{x,y} \quad (27)$$

where $F_{act}$ is the electrostatic force from the individual comb-finger actuators.

$$\therefore U_{x,y} = \pm\frac{F_e}{K_{x,y}} = \pm\frac{F_e}{4\left(\frac{2Eh_s w_s^3}{l_s^3}\right) + \left(\frac{2Eh_t w_t^3}{l_t^3}\right)} = \quad (28)$$

-continued $$\pm 2 \frac{l\varepsilon t_f}{gs_f E\left[4h_s\left(\frac{w_s}{l_s}\right)^3 + h_t\left(\frac{w_t}{l_t}\right)^3\right]} V^2$$

This in-plane (X-Y) displacement of the stage 2 caused by the pull-pull mode of the comb-drive actuators 6 represents the maximum motion achievable at particular voltages.

A matrix model for in-plane grid stiffness of the single-unit manipulator 1 will now be discussed.

Figure 23:
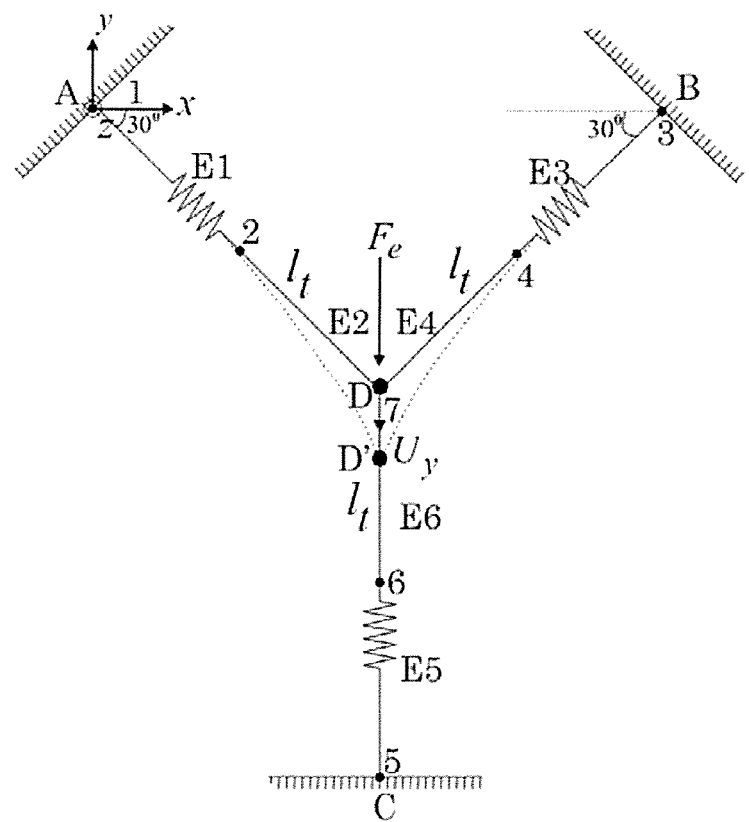
FIG. 23 illustrates a mechanical system representing a single-unit manipulator for the purpose of stiffness modelling, in accordance with various embodiments.

We compute the in-plane displacement of the stage 2 (from D to D') shown in FIG. 23 due to electrostatic force $F_e$, due to an electric field when voltage V is applied to the comb-drive actuators such as at node 23C. We form an equivalent grid stiffness matrix of the tethers 5 and spring flexure beams 9. The schematic of the manipulator 1 is divided into seven nodes, 23-1 to 23-7 and six elements 23-E1 to 23-E6, each corresponding to a beam structure, as shown in FIG. 23.

The element stiffness, $[k]_2$, $[k]_4$, $[k]_6$ of the tethers 21-E2, 21-E4 and 21-E6 inclined at an angle of 120° to each other is given by, $$[k]_2, [k]_4, [k]_6 = \frac{12EI}{l_t^3}\begin{bmatrix} s^2 & -cs & -s^2 & cs \\ -cs & c^2 & cs & -c^2 \\ -s^2 & cs & -s^2 & -cs \\ cs & -c^2 & -cs & c^2 \end{bmatrix} \quad (29)$$

Similarly, the element stiffness, $[k]_1$, $[k]_3$, $[k]_5$ of the spring flexure beams 21-E1, 21-E3 and 21-E5 is given by, $$[k]_1, [k]_3, [k]_5 = \frac{8Eh_sw^3}{l_s^3}\begin{bmatrix} c^2 & cs & -c^2 & -cs \\ cs & s^2 & -cs & -s^2 \\ -c^2 & -cs & -c^2 & cs \\ -cs & -s^2 & cs & s^2 \end{bmatrix} \quad (30)$$

where c=cos $\theta_n$ and s=sin $\theta_n$, $\theta_3=\theta_4=60°$, $\theta_1=\theta_2=120°$, $\theta_5=\theta_6=240°$ and the subscripts indicate the corresponding element number. I is the second moment of inertia of the beam.

After adding the terms of the individual element stiffness matrices into their corresponding locations in the global stiffness matrix[K], the total 14×14 stiffness matrix is, $$[K]_{eq} = \underbrace{\frac{8Ehw^3}{l_s^3}\begin{bmatrix} c^2 & cs & -c^2 & -cs \\ cs & s^2 & -cs & -s^2 \\ -c^2 & -cs & -c^2 & cs \\ -cs & -s^2 & cs & s^2 \end{bmatrix} + [k]_3 + [k]_5 +}_{Spring} \quad (31)$$

$$\underbrace{\frac{12EI}{l_t^3}\begin{bmatrix} s^2 & -cs & -s^2 & cs \\ -cs & c^2 & cs & -c^2 \\ -s^2 & cs & -s^2 & -cs \\ cs & -c^2 & -cs & c^2 \end{bmatrix} + [k]_2 + [k]_4}_{Tethering}$$

Each 4×4 matrix of Equation (31) when added and assembled generates the appropriate 14×14 stiffness matrix on the left hand side. Therefore the two sides are equivalent to each other and not equal due to the different orders of matrix of both sides before assembly.

Therefore writing the total structure stiffness equation accounting for the applied electrostatic force on nodes 7 and 5 and force and displacement boundary constraints at the other nodes, $$\begin{bmatrix} F_{1x} \\ F_{1y} \\ F_{2x} \\ F_{2y} \\ F_{3x} \\ F_{3y} \\ F_{4x} \\ F_{4y} \\ F_{5x} \\ F_{5y} = F_e \\ F_{6x} \\ F_{6y} \\ F_{7x} \\ F_{7y} = F_e \end{bmatrix} = [K]_{14\times 14}\begin{bmatrix} U_{1x} \\ U_{1y} \\ U_{2x} \\ U_{2y} \\ U_{3x} \\ U_{3y} \\ U_{4x} \\ U_{4y} \\ U_{5x} \\ U_{5y} = U_y \\ U_{6x} \\ U_{6y} \\ U_{7x} \\ U_{7y} = U_y \end{bmatrix} \quad (32)$$

Thus, the final displacement can be found by solving Equation (31), $$\therefore [U_y] = [K^{-1}]_{14\times 14}[F_e] \quad (33)$$

The model includes angular components in a mathematical treatment. Thus, a transformation matrix can be used to transform the local displacement components into global ones and this result in the global stiffness matrix.

In-plane slope-deflection model of the single-unit manipulator will now be described.

Figure 24:
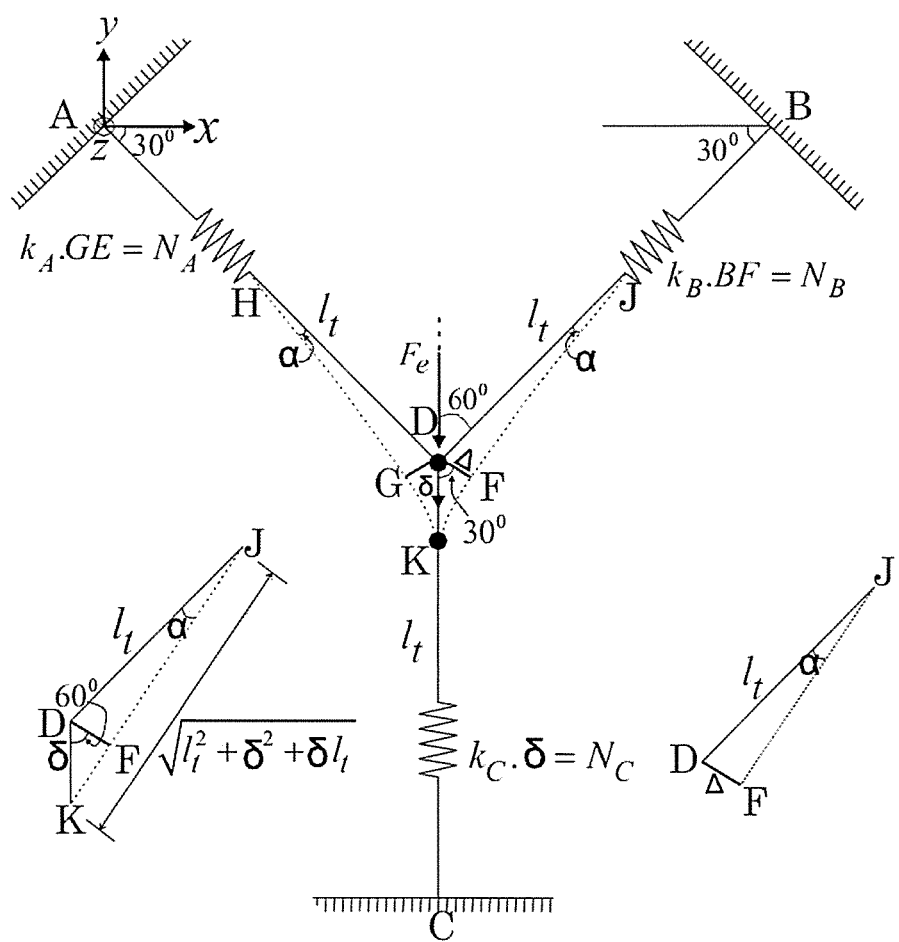
FIG. 24 illustrates a mechanical system representing a single-unit manipulator for the purpose of stiffness modelling, in accordance with various embodiments.

The in-plane motion of the single-unit manipulator 1 is also analytically modelled using slope-deflection equations, shown in FIG. 24, as an additional tool to investigate the design of the actuator. In this case, all the joints are considered rigid and the angle between the beams at the joints is constant under the loading. The distortion due to axial and shear stresses are considered negligible. Each side A, B and C consists of an arrangement of comb-drives 11 and spring flexure beams 9 which are connected to stage 2 represented in FIG. 24 as 24-D. The tethering beam length is $l_t$ and the angle between the corresponding tethering beams is 120°. When voltage V is applied to the comb drives 11 on side C, the tethering beams connected to A and B are displaced sideways by $\Delta$, vertically by $\delta$ and by an angle $\alpha$. Thus, the electrostatic force due to the comb-drive actuators in side C in terms of the slopes, deflection and stiffness of the component beams is, $$F_e = \frac{8l_tEh_sw_s^3}{l_s^3}\frac{\sin^2\alpha}{(6-8\sin^2\alpha)}\left(1 \pm \sqrt{-3\left(1+\frac{1}{\sin^2\alpha}\right)}\right) + \quad (34)$$

$$\frac{2Eh_sw_s^3}{l_s^3}\left(\sqrt{l_t^2+\delta^2+\delta l_t} - \frac{4l_t}{3\cos\alpha+\sqrt{3}\sin\alpha}\right) -$$

$$24\sqrt{3}\frac{EI}{l_t^2}\frac{\sin\alpha}{\sqrt{3}\cos\alpha+\sin\alpha}$$

Thus, the effective in-plane stiffness of the actuator is, $$K_{x,y} = \quad (35)$$

$$\left[\frac{4Eh_2w_s^3\sin\alpha\left(1 \pm \sqrt{-3\left(1+\frac{1}{\sin^2\alpha}\right)}\right)(\sqrt{3}\cos\alpha+\sin\alpha)}{l_s^3(6-8\sin^2\alpha)} + \frac{Eh_sw_s^3}{l_s^3l_t\sin\alpha}\right.$$

-continued $$\left(\sqrt{3}\cos\alpha + \sin\alpha\right)\left(\sqrt{l_t^2 + \delta^2 + \delta l_t} - \frac{4l_t}{3\cos\alpha + \sqrt{3}\sin\alpha}\right) - \frac{12\sqrt{3}\,EI}{l_t^3}\right]$$

This analytical derivation gives a different perspective on calculating the effective in-plane stiffness compared with the stiffness matrix approach discussed before.

Figure 25A:
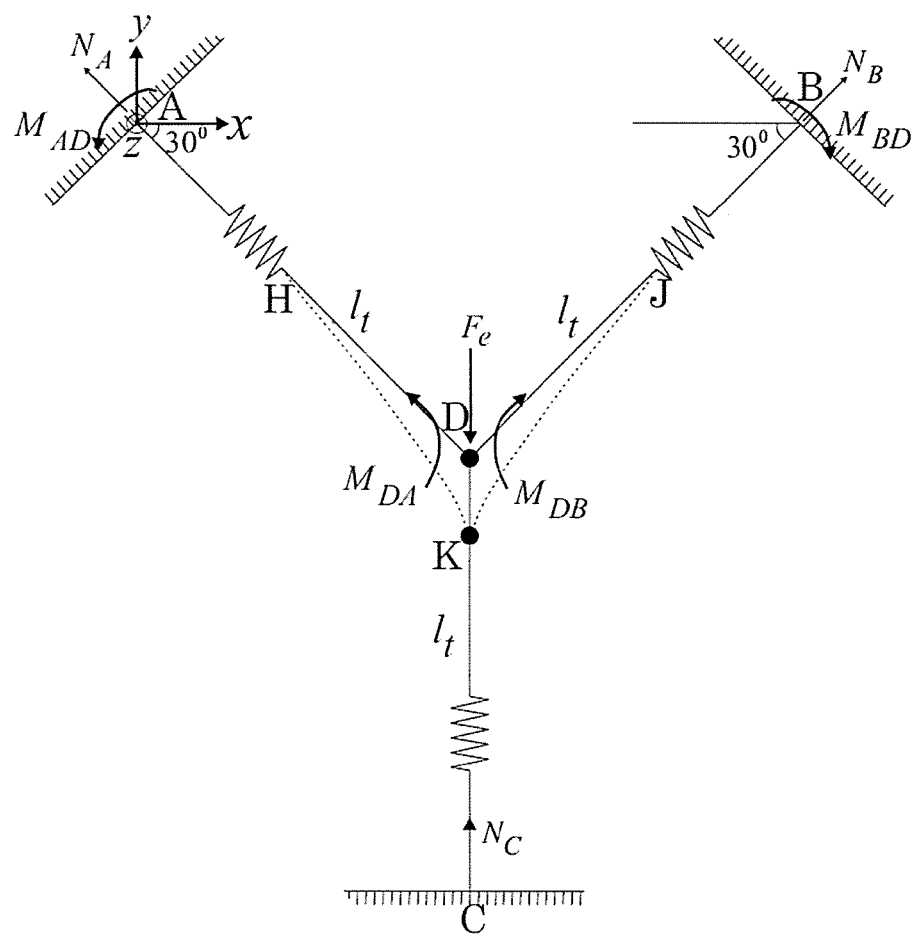
FIGS. 25a and 25b illustrate a mechanical system representing a single-unit manipulator for the purpose of stiffness modelling, in accordance with various embodiments.
Figure 25B:
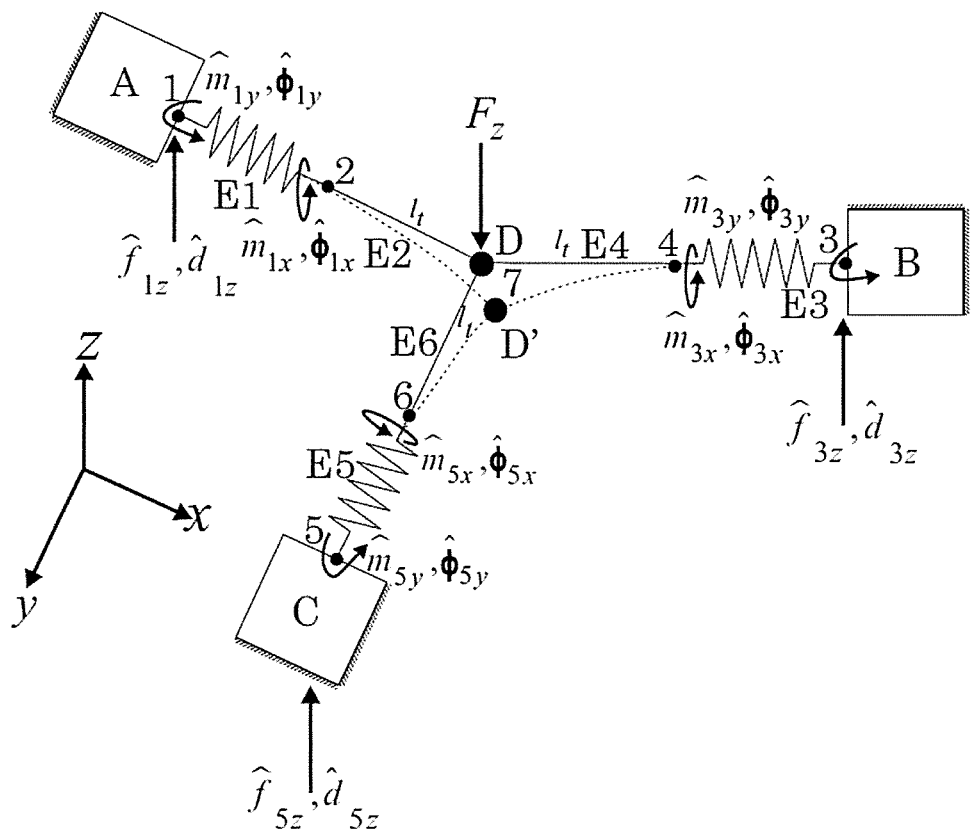

To compute the out-of-plane stiffness value as shown in FIGS. 25a and 25b, it is assumed that the stage 23-D has a unit displacement due to the motion of the comb-drive actuators on side C.

The final connectivity matrix becomes, $$\begin{Bmatrix} F_i \\ F_{i+1} \\ F_{i+2} \\ \ldots \\ \ldots \\ \ldots \\ \ldots \\ \ldots \\ F_j \end{Bmatrix} = \begin{bmatrix} k_{i,i}^m & k_{i,i+1}^m & k_{i,i+2}^m & \ldots & \ldots & \ldots & \ldots & \ldots & k_{i,j}^m \\ k_{i+1,i}^m & k_{i+1,i+1}^m & k_{i+1,i+2}^m & \ldots & \ldots & \ldots & \ldots & \ldots & k_{i+1,j}^m \\ k_{i+2,i}^m & k_{i+2,i+1}^m & k_{i+2,i+1}^m & \ldots & \ldots & \ldots & \ldots & \ldots & k_{i+2,j}^m \\ \ldots & \ldots & \ldots & \ldots & \ldots & \ldots & \ldots & \ldots & \\ \ldots & \ldots & \ldots & \ldots & \ldots & \ldots & \ldots & \ldots & \\ \ldots & \ldots & \ldots & \ldots & \ldots & \ldots & \ldots & \ldots & \\ \ldots & \ldots & \ldots & \ldots & \ldots & \ldots & \ldots & \ldots & \\ k_{j,i}^m & k_{j,i+1}^m & k_{j,i+2}^m & \ldots & \ldots & \ldots & \ldots & \ldots & k_{j,j}^m \end{bmatrix}_{21\times 21} \begin{Bmatrix} U_i \\ U_{i+1} \\ U_{i+2} \\ \ldots \\ \ldots \\ \ldots \\ \ldots \\ \ldots \\ U_j \end{Bmatrix} \quad (36)$$

Thus, the final connectivity stiffness matrix equation is, $$\begin{Bmatrix} F_{iz} \\ M_{ix} \\ M_{iy} \\ \ldots \\ F_{jz} \\ M_{jx} \\ M_{jy} \end{Bmatrix}_{21\times 21} = [K]_{21\times 21} \begin{Bmatrix} U_{iz} \\ \phi_{ix} \\ \phi_{iy} \\ \ldots \\ U_{jz} \\ \phi_{jx} \\ \phi_{jy} \end{Bmatrix}_{21\times 21} \quad (37)$$

Thus, the vertical out-of-plane displacement is, $$[U_z] = [K^{-1}]_{21\times 21}[F_z] \quad (38)$$

It should be appreciated that the tethers 5 may be beams or may be treated analytically as beams.

In accordance with the various embodiments disclosed, the middle layer of the silicon-on-wafer, of which the multiple-needle manipulator 130 is formed, is in the range of a few tenths of a micron to a few microns thick.

The forces and movement discussed here in with reference to the various embodiments may be dynamic and may involve or rely on mechanical resonance.

RECITATION OF EMBODIMENTS

Embodiment 1

A device comprising a cell trap comprising a plurality of micro-chambers, each micro-chamber configured to hold a cell; and a manipulator array comprising a plurality of manipulators, each manipulator in spatial communication with a respective micro-chamber, wherein each manipulator comprises a needle, a stage, and an actuator, wherein the needle is mounted to the stage, and the actuator is operable to apply force to the stage in a direction to move the needle to penetrate a cell in the respective micro-chamber.

Embodiment 2

The device of Embodiment 1, wherein each manipulator comprises a plurality of actuators operable to apply a plurality of forces to the stage in a plurality of directions to move the needle.

Embodiment 3

The device of any of the preceding Embodiments, wherein the manipulator array comprises a plurality of sub-arrays, each sub-array comprising a portion of the plurality of manipulators.

Embodiment 4

The device of Embodiment 3, wherein at least one sub-array of the plurality of manipulators is three-sided.

Embodiment 5

The device of any one of Embodiments 3 and 4, wherein at least one sub-array substantially forms a triangle.

Embodiment 6

The device of any of the preceding Embodiments, the manipulator array further comprising an interconnect, wherein the interconnect comprises connections to the actuator.

Embodiment 7

The device of any of the preceding Embodiments, the manipulator array further comprising a plurality of interconnects, wherein each interconnect comprises connections to the actuator, and wherein each interconnect is associated with a manipulator.

Embodiment 8

The device of any of Embodiments 6 and 7, the interconnect comprising a local interconnect, a transitional interconnect and a universal interconnect, wherein the universal interconnect is connected to the transitional interconnect, and the transitional interconnect is connected to the local interconnect.

Embodiment 9

The device of any of Embodiments 6 to 8, wherein the interconnect is located substantially at a side of the manipulator array.

Embodiment 10

The device of any of Embodiments 3 to 8, wherein the sub-arrays are arranged to substantially form a hexagon.

Embodiment 11

The device of any of Embodiments 6 to 10, wherein the interconnect is located substantially at a periphery of the manipulator array.

Embodiment 12

A manipulator array comprising a substrate; a plurality of manipulators arranged on the substrate, each manipulator comprising a needle, a stage, a tether, and an actuator, wherein the needle is mounted to the stage, the stage is connected to the actuator by the tether, and the actuator is operable to apply tension in at least one axis to actuate the stage in a direction to manipulate the needle; and a plurality of sub-arrays, each sub-array comprising a portion of the plurality of manipulators, and interconnects formed on each side of each sub-array, wherein the plurality of sub-arrays are arranged together on the substrate with at least a portion of the interconnects located at a periphery of the manipulator array.

Embodiment 13

The array of Embodiment 12, wherein each manipulator comprises a plurality of actuators operable to apply tension in more than one axis to actuate the stage in a direction to manipulate the needle.

Embodiment 14

The array of any of Embodiments 12 and 13, wherein at least one sub-array of the plurality of manipulators is three-sided.

Embodiment 15

The array of any of Embodiments 12 to 14, wherein at least one sub-array substantially forms a triangle.

Embodiment 16

The array of any of Embodiments 12 to 15, wherein the interconnects comprise connections to the actuator, and wherein each interconnect is associated with a manipulator.

Embodiment 17

The array of any of Embodiments 12 to 16, the interconnects comprising a local interconnect, a transitional interconnect and a universal interconnect, wherein the universal interconnect is connected to the transitional interconnect, and the transitional interconnect is connected to the local interconnect.

Embodiment 18

The array of any of Embodiments 12 to 17, wherein the sub-arrays are arranged to substantially form a hexagon.

Embodiment 19

The array of any of Embodiments 13 to 18, wherein the plurality of actuators are operable to apply tension in three directions.

Embodiment 20

The array of any of Embodiments 13 to 19, wherein the plurality of actuators is operable to provide tensile forces.

Embodiment 21

The array of any of Embodiments 12 to 20, wherein the manipulator array is operable to receive applied voltages at the interconnect, the voltages generating electrostatic forces to cause the actuator to apply tension so as to actuate the stage parallel to a plane parallel with the manipulator array to manipulate the needle.

Embodiment 22

The device of any of Embodiments 12 to 21, wherein the manipulator array is operable to receive applied voltages at the interconnect, the voltages generating electrostatic forces to cause the actuator to apply tension so as to actuate the stage transverse to a plane parallel with the manipulator array to manipulate the needle.

Embodiment 23

The device of any of Embodiments 12 to 22, wherein the manipulator array is operable to receive applied voltages at the interconnect at a periphery of the device, the voltages generating electrostatic forces to cause the actuator to apply forces so as to actuate the stage parallel to a plane parallel with the manipulator to move the needle with respect to the associated micro-chamber of the cell trap.

Embodiment 24

The device of any of Embodiments 12 to 23, wherein the manipulator array is operable to receive applied voltages at the interconnect at a periphery of the device, the voltages generating electrostatic forces to cause the actuator to apply forces so as to actuate the stage transverse to a plane parallel with the manipulator to move the needle with respect to the associated micro-chamber of the cell trap.

In the preceding description and the following claims the word "comprise" or equivalent variations thereof is used in an inclusive sense to specify the presence of the stated feature or features. This term does not preclude the presence or addition of further features in various embodiments.

It is to be understood that the present invention is not limited to the embodiments described herein and further and additional embodiments within the spirit and scope of the invention will be apparent to the skilled reader from the examples illustrated with reference to the drawings. In particular, the invention may reside in any combination of features described herein, or may reside in alternative embodiments or combinations of these features with known equivalents to given features. Modifications and variations of the example embodiments of the invention discussed above will be apparent to those skilled in the art and may be made without departure of the scope of the invention as defined in the appended claims.

The invention claimed is:

1. A manipulator array comprising:
   a substrate;
   a plurality of manipulators arranged on the substrate, each manipulator comprising a needle, a stage, a tether, and an actuator, wherein the needle is mounted to the stage, the stage is connected to the actuator by the tether, and the actuator is operable to apply tension in at least one axis to actuate the stage in a direction to manipulate the needle; and
   a plurality of sub-arrays, each sub-array comprising a portion of the plurality of manipulators, and interconnects formed on each side of each sub-array, wherein the plurality of sub-arrays are arranged together on the substrate with at least a portion of the interconnects located at a periphery of the manipulator array.

2. The manipulator array of claim 1, wherein each manipulator comprises a plurality of actuators operable to apply tension in more than one axis to actuate the stage in a direction to manipulate the needle.

3. The manipulator array of claim 1, wherein at least one sub-array of the plurality of manipulators is three-sided.

4. The manipulator array of claim 1, wherein the interconnects comprise connections to the actuator, and wherein each interconnect is associated with a manipulator.

5. The manipulator array of claim 1, the interconnects comprising a local interconnect, a transitional interconnect and a universal interconnect, wherein the universal interconnect is connected to the transitional interconnect, and the transitional interconnect is connected to the local interconnect.

6. The manipulator array of claim 2, wherein the plurality of actuators are operable to apply tension in three directions.

7. The manipulator array of claim 1, wherein the plurality of actuators are operable to provide tensile forces.

8. The manipulator array of claim 1, wherein the manipulator array is operable to receive applied voltages at the interconnect, the voltages generating electrostatic forces to cause the actuator to apply tension so as to actuate the stage parallel to a plane parallel with the manipulator array to manipulate the needle.

9. The manipulator array of claim 1, wherein the manipulator array is operable to receive applied voltages at the interconnect, the voltages generating electrostatic forces to cause the actuator to apply tension so as to actuate the stage transverse to a plane parallel with the manipulator array to manipulate the needle.

10. The manipulator array of claim 1, wherein the manipulator array is operable to receive applied voltages at the interconnect at a periphery of the device, the voltages generating electrostatic forces to cause the actuator to apply forces so as to actuate the stage parallel to a plane parallel with the manipulator to move the needle with respect to the associated micro-chamber of the cell trap.

11. The manipulator array of claim 1, wherein the manipulator array is operable to receive applied voltages at the interconnect at a periphery of the device, the voltages generating electrostatic forces to cause the actuator to apply forces so as to actuate the stage transverse to a plane parallel with the manipulator to move the needle with respect to the associated micro-chamber of the cell trap.

12. A device comprising:
    the manipulator array of claim 1; and
    a cell trap comprising a plurality of micro-chambers, each micro-chamber configured to hold a cell.

13. The device of claim 12, wherein each manipulator of the manipulator array is in spatial communication with a respective micro-chamber and wherein the actuator of each manipulator is operable to apply force to the respective stage in a direction to move the respective needle to penetrate a cell in the respective micro-chamber.

* * * * *